(12) United States Patent
Bischof et al.

(10) Patent No.: US 10,725,033 B2
(45) Date of Patent: Jul. 28, 2020

(54) LATERAL FLOW ASSAYS WITH THERMAL CONTRAST READERS

(71) Applicants: Regents of the University of Minnesota, Minneapolis, MN (US); The Governing Council of the University of Toronto, Toronto (CA)

(72) Inventors: John C. Bischof, St. Paul, MN (US); Zhenpeng Qin, Allen, TX (US); Warren Chan, Toronto (CA); Taner Akkin, Arden Hills, MN (US); Li Zhan, Minneapolis, MN (US)

(73) Assignees: REGENTS OF THE UNIVERSITY OF MINNESOTA, Minneapolis, MN (US); THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 57 days.

(21) Appl. No.: 15/802,120

(22) Filed: Nov. 2, 2017

(65) Prior Publication Data
US 2018/0128827 A1    May 10, 2018

Related U.S. Application Data

(63) Continuation-in-part of application No. 15/584,301, filed on May 2, 2017, which is a continuation-in-part
(Continued)

(51) Int. Cl.
*G01N 33/543* (2006.01)
*G01N 33/558* (2006.01)
(Continued)

(52) U.S. Cl.
CPC ..... *G01N 33/54393* (2013.01); *G01N 21/171* (2013.01); *G01N 21/77* (2013.01);
(Continued)

(58) Field of Classification Search
None
See application file for complete search history.

(56) References Cited

U.S. PATENT DOCUMENTS

| 4,094,647 A | 6/1978 | Deutsch et al. |
| 4,313,734 A | 2/1982 | Leuvering |

(Continued)

FOREIGN PATENT DOCUMENTS

| CN | 101368907 A | 2/2009 |
| EP | 1225442 A2 | 7/2002 |

(Continued)

OTHER PUBLICATIONS

Office Action issued in related patent application No. KR 10-2014-7023705, dated Feb. 17, 2019.
(Continued)

*Primary Examiner* — Rebecca M Giere
(74) *Attorney, Agent, or Firm* — Westman, Champlin & Koehler, P.A.; Visala C. Goswitz

(57) ABSTRACT

Assays used in conjunction with a thermal contrast reader are disclosed. In the assay, the test strip includes materials that can develop a thermal response if a target analyte is present in a sample. Linear flow assays include nanoparticles with high affinity binding to the analyte. Binding of the nanoparticles with an analyte in the sample is detected using thermal contrast. Analytes over a broad range of concentrations are detected in the linear flow assays. Methods of detecting target analytes and kits comprising lateral flow assays and thermal contrast reader are also disclosed.

9 Claims, 30 Drawing Sheets

Related U.S. Application Data of application No. 14/375,294, filed as application No. PCT/US2013/023839 on Jan. 30, 2013, now Pat. No. 9,651,508.

(60) Provisional application No. 61/593,036, filed on Jan. 31, 2012.

(51) Int. Cl.
  *G01N 33/569* (2006.01)
  *G01N 33/76* (2006.01)
  *G01N 25/48* (2006.01)
  *G01N 21/77* (2006.01)
  *G01N 21/17* (2006.01)

(52) U.S. Cl.
  CPC ......... *G01N 25/488* (2013.01); *G01N 33/558* (2013.01); *G01N 33/5695* (2013.01); *G01N 33/56905* (2013.01); *G01N 33/56961* (2013.01); *G01N 33/76* (2013.01); *G01N 2021/1714* (2013.01); *G01N 2333/35* (2013.01); *G01N 2333/39* (2013.01); *G01N 2333/445* (2013.01); *G01N 2333/59* (2013.01); *Y02A 50/58* (2018.01)

(56) References Cited

U.S. PATENT DOCUMENTS

| | | | |
|---|---|---|---|
| 4,857,453 | A | 8/1989 | Ullman et al. |
| 5,073,484 | A | 12/1991 | Swanson et al. |
| 5,110,910 | A | 5/1992 | Tsav |
| 5,559,041 | A | 9/1996 | Kang et al. |
| 5,571,726 | A | 11/1996 | Brooks, Jr. et al. |
| 5,578,577 | A | 11/1996 | Ching et al. |
| 5,591,645 | A | 1/1997 | Rosenstein |
| 6,187,598 | B1 | 2/2001 | May et al. |
| 6,352,862 | B1 | 3/2002 | Davis et al. |
| 6,485,982 | B1 | 11/2002 | Charlton |
| 7,297,529 | B2 | 11/2007 | Polito et al. |
| 7,314,763 | B2 | 1/2008 | Song et al. |
| 7,371,582 | B2 | 5/2008 | Nahm et al. |
| 8,021,848 | B2 | 9/2011 | Straus |
| 8,034,397 | B2 | 10/2011 | Yang et al. |
| 8,105,843 | B2 | 1/2012 | Buchanan |
| 8,128,871 | B2 | 3/2012 | Petruno et al. |
| 8,153,444 | B2 | 4/2012 | Kirkegaard et al. |
| 2003/0119202 | A1 | 6/2003 | Kaylor et al. |
| 2003/0143580 | A1 | 7/2003 | Straus |
| 2004/0180369 | A1 | 9/2004 | Franzen et al. |
| 2008/0032420 | A1 | 2/2008 | Lambert |
| 2008/0095714 | A1 | 4/2008 | Castella |
| 2008/0102473 | A1 | 5/2008 | Fouquet et al. |
| 2009/0211345 | A1 | 8/2009 | Nahm et al. |
| 2009/0305231 | A1* | 12/2009 | Weidemaier ............. B82Y 5/00 435/5 |
| 2010/0136566 | A1 | 6/2010 | Mehra et al. |
| 2012/0258881 | A1 | 10/2012 | Schwartz et al. |

FOREIGN PATENT DOCUMENTS

| | | |
|---|---|---|
| EP | 1 933 147 | 8/2011 |
| JP | 2001-507464 A | 6/2001 |
| WO | WO 00/31539 | 6/2000 |
| WO | WO 03/060461 | 7/2003 |
| WO | WO 03/073817 | 9/2003 |
| WO | WO 2004/092715 | 10/2004 |
| WO | WO 2007/090058 | 8/2007 |
| WO | WO 2007/135613 | 11/2007 |
| WO | WO 2008/067079 | 6/2008 |
| WO | WO 2009/152209 | 12/2009 |

OTHER PUBLICATIONS

Nearingburg B et al. "Characterization of surface plasmon energy transduction in gold nanoparticle/polymer composite by photo-DSC", Thermochimica Acta, Elsevier Science Publishers, Amsterdam, NL, vol. 512, No. 1-2, ISSN 0040-6031 (Jan. 10, 2011).

Hongwei Liao et al. "Biomedical applications of plasmon resonant metal nanoparticles", Nanomedicine, (Aug. 1, 2006), vol. 1, No. 2, doi:10.2217/17435889.1.2.201, ISSN 1743-5889, pp. 201-208, XP055092689.

Communication of a Notice of Opposition dated Sep. 14, 2018 and Notice of Opposition to EP Patent No. 2810052 filed Sep. 6, 2018.

"A Colorimetric Gold Nanoparticle Sensor to Interrogate Biomolecular Interactions in Real Time on a Surface", by Nath et al., Analytical Chemistry, vol. 74, No. 3, Feb. 1, 2002.

"A Fast and Sensitive Quantitative Lateral Flow Immunoassay for Cry1Ab Based on a Novel Signal Amplification Conjugate", by Chen et al., Sensors, 2012.

"A Lateral Flow Assay for Quantitative Detection of Amplified HIV-1 RNA", by Rohrman et al., PLOS ONE, vol. 7, Issue 9, Sep. 2012.

"Photothermal Multispectral Image Cytometry for Quantitative Histology of Nanoparticles and Micrometastasis in Intact, Stained and Selectively Burned Tissues", by Nedosekin et al., Cytometry Part A, 2010.

"Detection of DNA Hybridization on Indium Tin Oxide Surfaces", by Moses et al., Sensors and Actuators B, 2007.

"Development of Gold Nanorod Lateral Flow Test for Quantitative Multi-Analyte Detection", by Venkataramasubramani et al., IFMBE Proceedings 24, 2009.

"Direct Measurements of Heating by Electromagnetically Trapped Gold Nanoparticles on Supported Lipid Bilayers", by Bendix et al., ACSNANO, vol. 4, No. 4, Apr. 6, 2010.

"Discerning Trends in Multiplex Immunoassay Technology with Potential for Resource-Limited Settings", by Gordon et al., Clinical Chemistry 58:4, 2012.

"Gold and Silican-Coated Gold Nanoparticles as Thermographic Labels for DNA Detection", by Cerruti et al., Analytical Chemistry, vol. 78, No. 10, May 15, 2006.

"Enhancement of the Detection Limited for Lateral Flow Immunoassays: Evaluation and Comparison of Bioconjugates", by Linares et al., Journal of Immunological Methods, 2012.

"Lateral Flow (immuno)assay: its Strengths, Weaknesses, Opportunities and Threats. A Literature Survey", by Posthuma-Trumpie et al., Anal Bioanal Chem., 2009.

"Gold Nanoparticles in Biology and Medicine: Recent Advances and Prospects", by Dykman et al., Acta Naturae, vol. 3, No. 2, 2011.

"Room-Temperature Detection of a Single Molecule's Absorption by Photothermal Contrast", by Yorulmaz et al., Science, vol. 330, Oct. 15, 2010.

"Significantly Improved Analytical Sensitivity of Lateral Flow Immunoassays by Thermal Contrast", by Qin et al., Angew Chem Int Ed Engl., Apr. 27, 2012.

"Chapter 1 Evolution in Lateral Flow-Based Immunoassay Systems", by O'Farrell, Lateral Flow Immonoassay, 2009.

"Chapter 5 Colloidal Gold and Other Labels for Lateral Flow Immunoassays", by Chun, Lateral Flow Immunoassay, 2009.

"Chapter 9 Handheld and Portable Reader Devices for Lateral Flow Immunoassays", by Faulstich et al., Lateral Flow Immunoassay, 2009.

"Thermophysical and Biological Responses of Gold Nanoparticle Laser Heating", by Qin et al., Chem. Soc. Rev., 2012.

"Ultrasensitive Heterogeneous Immunoassay Using Photothermal Deflection Spectroscopy. 2. Quantitation of Ultratrace Carcinoembryonic Antigen in Human Sera", by Kimura et al., Analytical Chemistry, vol. 68, No. 17, Sep. 1, 1996.

Notification of Transmittal of the International Search Report and the Written Opinion of the International Searching Authority, or the Declaration, PCT/US2013/023839, dated Sep. 4, 2013.

Office Action issued in corresponding Chinese Patent application No. 201380016094.5 dated Feb. 29, 2016.

(56) References Cited

OTHER PUBLICATIONS

Nalinthya, Elizabeth et al. "Evolution of Cryptococcal Antigen Testing: What is New?" Current Fungal Infection Reports, Springer US, Boston, vol. 10, No. 2, Apr. 12, 2016, pp. 62-67.
Extended European Search Report issued for EP Application No. 17204410.9, dated Feb. 19, 2018.

* cited by examiner

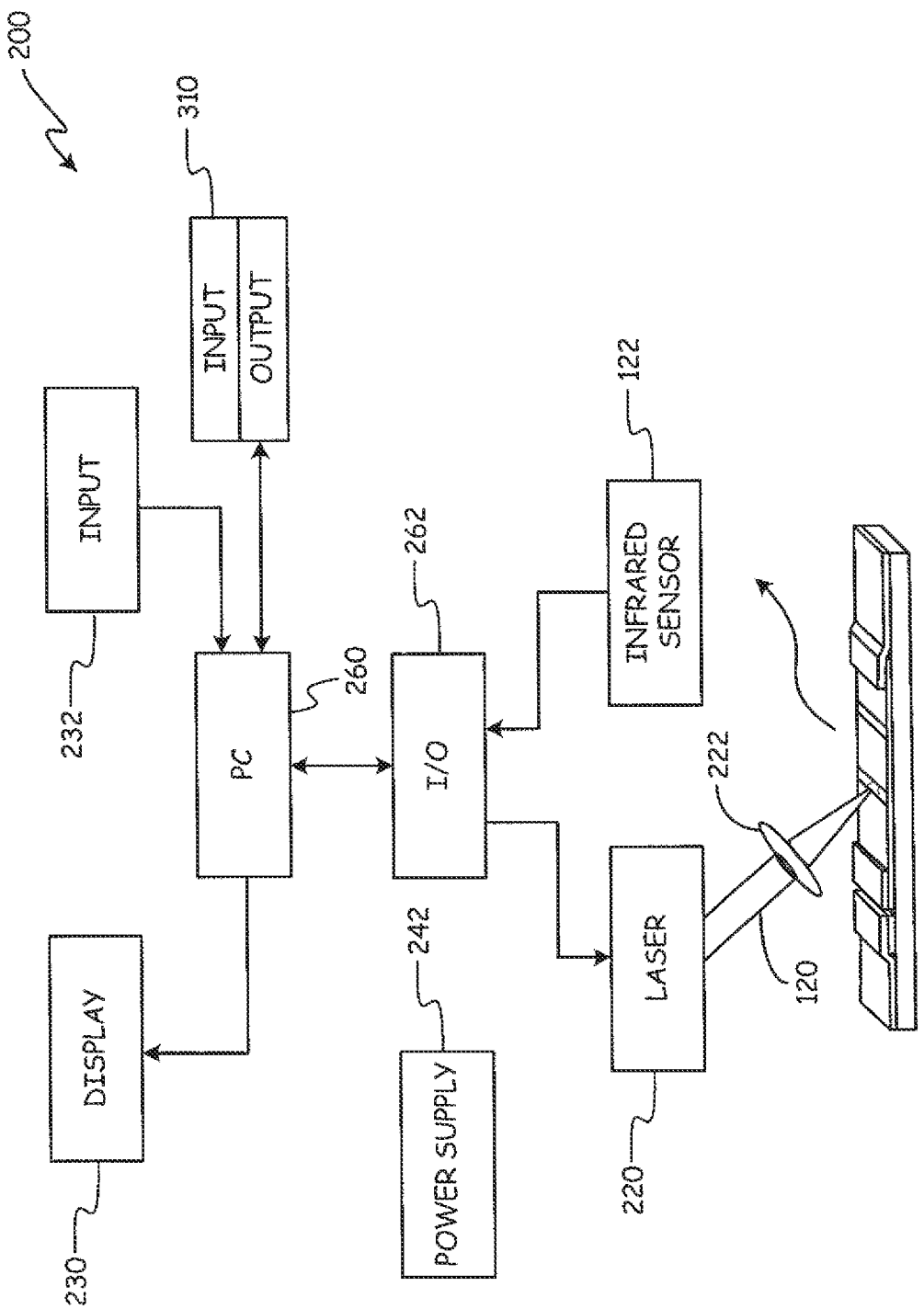

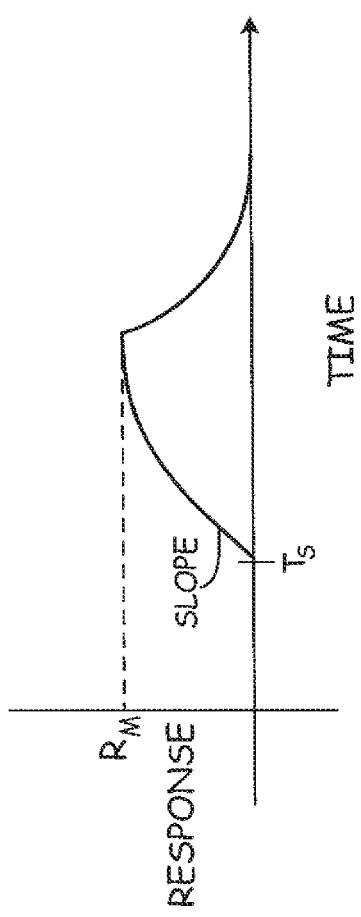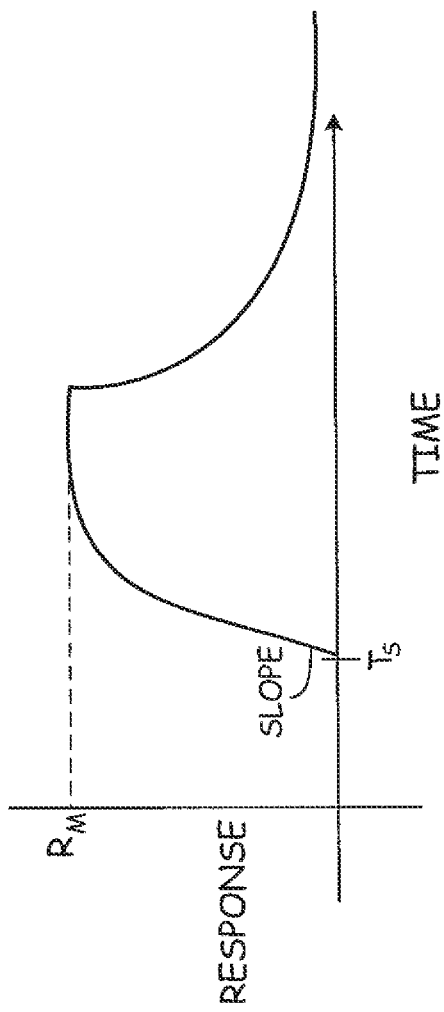

Synthesized
29.8nm (±2.9nm)

hCG dipstick
D=32.2nm (±6.4nm)

CM* dipstick
D=25.3nm (±5.5nm)

*CM: cryptococcal meningitis

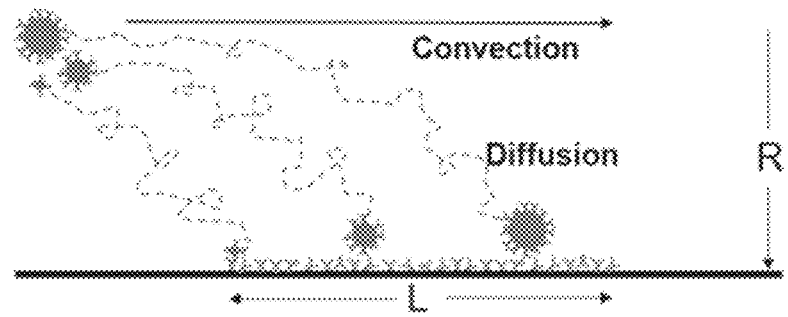
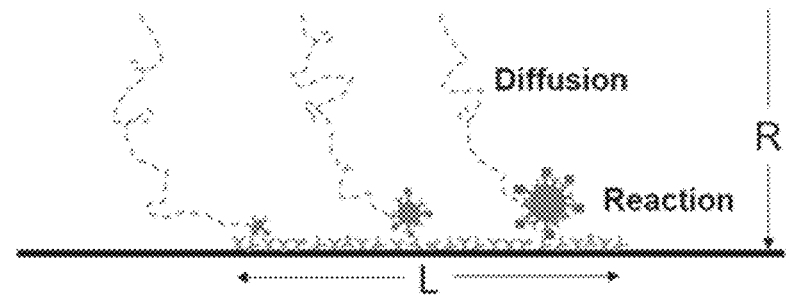
Figure 14A
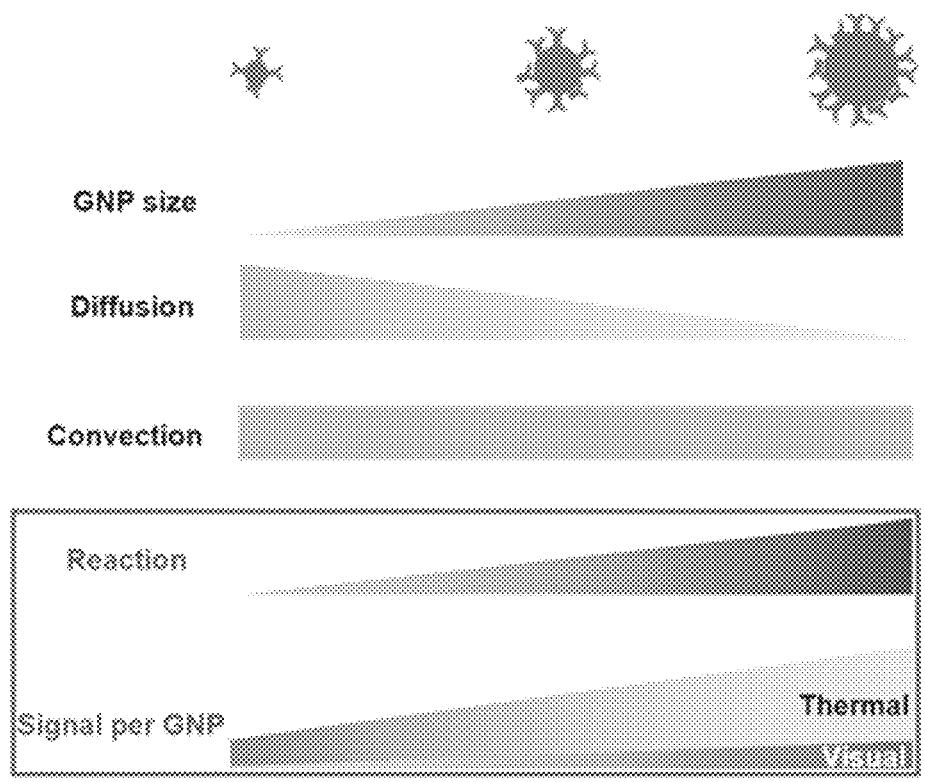
Figure 14B

LATERAL FLOW ASSAYS WITH THERMAL CONTRAST READERS

CROSS-REFERENCE TO RELATED APPLICATIONS

The present application is a Continuation in Part of and claims priority of U.S. patent application Ser. No. 15/584,301, filed May 2, 2017, which is a Continuation in Part of and claims priority of U.S. patent application Ser. No. 14/375,294, filed Jul. 29, 2014, which is a Section 371 National Stage Application of International Application Number PCT/US2013/023839, filed Jan. 30, 2013, and published as WO 2013/116333 on Aug. 8, 2013, in English, which claims priority of U.S. Provisional Patent Application No. 61/593,036, filed on Jan. 31, 2012.

FIELD

The present invention relates to assays and readers for detecting analytes in a sample. More specifically, the present invention relates to assays and readers that operate based upon thermal contrast.

BACKGROUND

LFA (lateral flow assay, or lateral flow immunoassay, also called rapid diagnostic test—RDT, or bioassays) technology has found widespread use both in and out of laboratory settings. In a typical assay, a fluid sample from a patient is applied to a test strip. The sample interacts with chemicals on the test strip causing the strip to optically change characteristics. The visual indicator may be observed by a person, for example, using a home pregnancy test. However, more accurate readings can be obtained using an assay reader. Such a reader may, for example, include a sensitive optical sensor that is capable of sensing optical variations more accurately and in a more repeatable manner than a human viewer. One example of a typical assay reader is shown in U.S. Pat. No. 7,297,529, to Polito et al., issued Nov. 20, 2007.

The ability to rapidly identify diseases enables prompt treatment and improves outcomes. This possibility has increased the development and use of rapid point-of-care diagnostic devices or systems that are capable of biomolecular detection in both high-income and resource-limited settings. LFAs are inexpensive, simple, portable and robust, thus making LFAs commonplace in medicine, agriculture, and over-the-counter personal use, such as for pregnancy testing. LFAs are also widely used for a number of infectious diseases, such as malaria, AIDS-associated cryptococcal meningitis, pneumococcal pneumonia, and recently tuberculosis.

Although the analytical performance of some LFAs are comparable to laboratory-based methods, the analytical sensitivity (alternatively called limit of detection) of most LFAs is in the mM to μM range, which is significantly less sensitive than other molecular techniques such as enzyme-linked immmunoassays (ELISAs). As a consequence, LFAs are not particularly useful for early detection in a disease course when there is low level of antigen. Research has focused on developing microfluidics, biobarcodes and enzyme-based assay technologies to obtain higher sensitivity in antigen detection since these techniques may potentially detect in the nM to pM range. However, all of these methods are still in the development stage and have not been demonstrated for adoption in a reliable, cost-effective manner to use in a point-of-care site by an end user.

As is now well known, the optical, thermal and electrical properties of materials change dramatically in the nanoscale. In particular, the enhanced photothermal signature of metal nanoparticles have been utilized for: thermal ablation of malignant tumors, detecting circulating tumor cells, photothermal gene transfection, enhancing the therapeutic efficiency of chemotherapeutics, and for tracking the transport of nanoparticles within cells.

SUMMARY

In one aspect, the present description relates to a thermal contrast assay reader. The thermal contrast assay reader includes an energy source, a sensor, I/O circuitry and an opening to receive an assay strip. The reader is configured to convert the sensor results to an output signal upon activation of the energy source onto the test region of the assay strip.

In a further aspect, the present description relates to a method of detecting analytes in a sample comprising exposing the test region of a test strip in a lateral flow assay to an energy source after contacting the test strip of the assay with a sample. The sample moves through the test strip by capillary action and the assay comprises nanoparticles conjugated to analyte binding molecule that bind the analyte in the sample and a test region comprising capture molecules. The method also includes measuring the heat generated in the test region by a sensor to detect the presence or absence of the analyte in the test region.

In another aspect, the present description relates to a lateral flow assay comprising a sample pad, a test strip, nanoparticles conjugated to an analyte binding molecule, a test region, a control region and an absorbent pad configured for fluid communication when a sample is applied. The nanoparticles may be between about 10 nm and about 400 nm. The concentration range for detection of the analyte may be between about $10^{-5}$ mg/L and about 310 mg/L. The range of the concentration of the analyte detected may be between about 3 $\log_{10}$ to about 7 $\log_{10}$. The range of the concentrations of the analyte detected using visual and thermal detection may be up to about 6 orders of magnitude (6 $\log_{10}$) or more.

In yet a further aspect, the present description relates to method of enhancing the analytical performance of a LFA comprising optimizing the size and shape of the nanoparticles based on the binding affinity of the analyte to nanoparticles coated with the analyte binding molecules and the diffusion and convection of the nanoparticles in a membrane of the lateral flow assay and detecting the binding of the nanoparticles with the analyte by thermal contrast. The method also includes printing the LFA with the nanoparticles wherein the size of the nanoparticle is determined based on results from optimization, wherein the concentration range of the LFA for detecting an analyte in a sample is between about $10^{-5}$ mg/L and about 310 mg/L.

In yet another aspect, the present description relates to an assay kit comprising an LFA assay system. The assay kit comprising a sample pad, a test strip, nanoparticles conjugated to an analyte binding molecule, a test region, a control region and an absorbent pad configured for fluid communication when a sample is applied. The kit also includes a thermal contrast assay reader.

BRIEF DESCRIPTION OF THE DRAWINGS

FIG. 2B is simplified block diagram of a bench top assay reader.

FIGS. 4A and 4B are graphs illustrating the thermal response of a LFA versus time.

FIG. 14A is a diagram wherein Pe is the ratio of diffusion time to convection time of a GNP, Pe>>1 in LFA implies the transport is diffusion-limited, Da is the ratio of reaction flux to diffusion flux, Da<<1 in LFA implies the rate limit is reaction.

FIG. 14B is a diagram comparing 30 nm, 60 nm and 100 nm GNPs and indicates 100 nm GNPs can improve LFA sensitivity due to higher reaction rate and signal per GNP.

DETAILED DESCRIPTION

Figure 1:
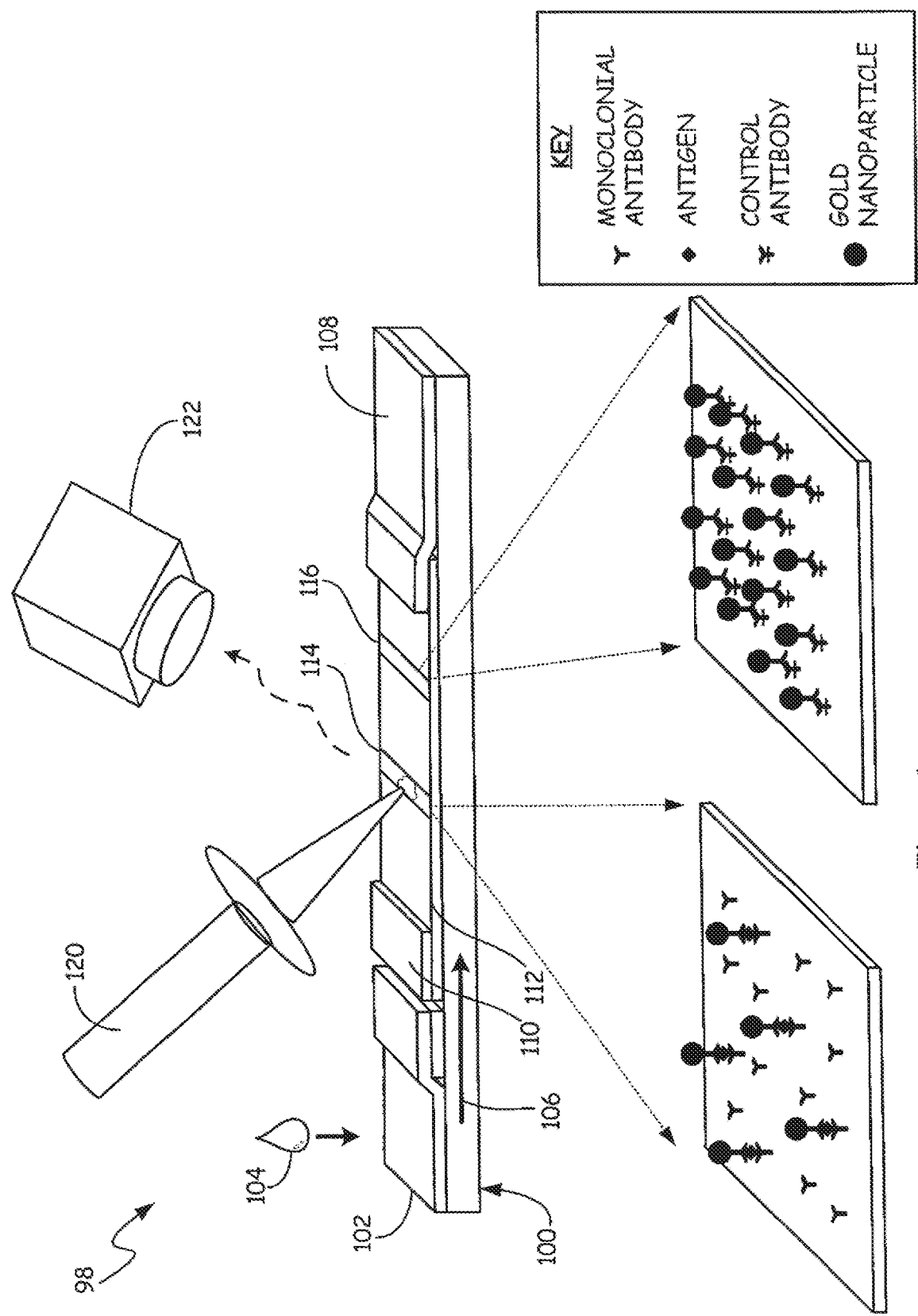
FIG. 1 is a simplified diagram showing a lateral flow assay test strip and reader system.

The present description includes assay systems that are used in conjunction with a thermal contrast reader. The present description can also include methods for detecting analytes in a sample using a thermal contrast assay and reader systems. The present description can include an assay test strip that can exhibit a thermal characteristic that changes in response to exposure to specific target compounds that may be present in a sample. The present description can further include a reader for reading the thermal properties of such a test strip. Aspects of the present description are discussed below in greater detail.

Thermal contrast assay systems are assays that are configured to work in conjunction with a thermal contrast reader. A thermal contrast assay system can be advantageously used to detect analytes in samples at much lower concentrations than assays using visual readers. The thermal contrast assay system can be a highly sensitive detection system for analytes in a variety of samples. This advantageously enables detection of diseases or conditions at a much earlier stage than comparable LFAs using visual detection methods. The thermal contrast assay system can also be used to detect analytes in samples at high concentrations. The thermal contrast assay systems described herein can be used to detect the concentration of the analytes that may be across a broad range of concentration. In addition, the simplicity of the method enables an end-user to use the system with ease and accuracy. This system can be highly amenable to point-of-care facilities and resource-limited settings. Embodiments described herein relate to thermal contrast assay systems that can be used to extend the sensitivity, dynamic range, and quantification of clinically used LFAs.

The present description also includes a kit wherein the kit includes a thermal contrast reader and an assay system described herein. The kit can be used by an end user to process a desired sample using the assay system and then to detect the target analyte and/or the quantity of the target analyte using the thermal contrast reader. The kit may include instructions related to the use of the kit.

The present description generally relates to laser excitation of nanoparticles, although it is understood that other embodiments with electromagnetic excitation are also within the scope of this invention. Laser (or light) excitation of nanoparticles as referred to herein relates to excitation of nanoparticles to produce heat that can be read by an infrared or other heat sensor with the understanding that other embodiments are also possible and within the scope of this invention. Diagnostic circuitry coupled to the sensor output is configured to provide a diagnostic output indication of a diagnostic condition of the patient as a function of the sensor output.

The assay systems described herein can be used to detect target analytes in a sample using nanoparticles conjugated with analyte binding molecules. Specifically, nanoparticles in assays can be used efficiently to convert incoming light to heat. In the assays, a membrane is contacted with a sample potentially containing an analyte. As the sample moves through the membrane, generally by capillary action, nanoparticles conjugated with the analyte binding molecules bind the target analyte to form a nanoparticle/analyte complex. "Nanoparticle/analyte complex" as used herein refers to nanoparticles conjugated to analyte binding molecules that have bound analyte from the sample. The nanoparticle/analyte complex continues to move through the membrane toward a test region containing capture molecules that bind the desired analyte. The nanoparticle/analyte complex is bound by the capture molecules and retained in the test region. A thermal contrast reader described herein can then be used to detect the presence or absence of the analyte. In addition, the thermal contrast reader can also quantitate the amount of analyte present in the test region and consequently, the sample. The thermal contrast reader generally includes a heat source and a heat sensor configured as described below.

An assay system, i.e. an LFA, generally includes a sample pad, a membrane, nanoparticles conjugated to an analyte binding molecule and capture molecules for the analyte. The LFA system may also include a conjugate pad, an absorbent pad, a backing, a test region, a control region and/or combinations of all of these components. The test region generally includes analyte capture molecules. The control region can include a control molecule such as a control antibody. The conjugate pad generally includes the nanoparticles conjugated to the analyte binding molecules.

"Membrane" as used herein refers to a test device or strip that employs a membrane and one or more reagents to detect the target analyte in the sample. "Membrane" and "test strip" may be used interchangeably.

Assays that can be used in conjunction with the thermal contrast reader include lateral flow assays. A variety of configurations for conducting lateral flow assays are known in the art and described, for example, in U.S. Patent Publication US 2003/0119202 by Kaylor et al. and US Patent Publication No. US 2010/0136566 by Mehra et al. and are incorporated herein by reference. FIG. 1 illustrates one exemplary embodiment and other configurations for conducting lateral flow assays are known in the art and also within the scope of the invention.

FIG. 1 is a simplified diagram showing an exemplary embodiment of a lateral flow assay test and reader system 98 in accordance with the present invention. A test strip 100 includes a sample pad 102 that is configured to receive a sample 104 from a patient. Capillary action causes the sample 104 to flow from the sample pad 102 in the direction indicated by arrow 106 towards absorbent pad 108. Sample 104 flows through a conjugate pad 110 and through a membrane 112 until it reaches a test region 114. A separate control region 116 is also provided. Test strip 100, sample pad 102, absorbent pad 108, conjugate pad 110, test region 114 and control region 116 are all in fluid communication. "Fluid communication" as used herein refers to the ability of liquid to flow or travel between the stated materials or surfaces.

As illustrated in the inset of FIG. 1, an exemplary embodiment of the test region can include gold nanoparticles associated with a monoclonal antibody bonded with the antigen at test region 114. The amount of bonded gold nanoparticles bonded in test region 114 can be determined by applying energy 120 causing heating of the test region 114. A thermal sensor 122 directed at the test region 114 measures the heating of the test region 114 that is related to the amount of nanoparticles and therefore the amount of antigens present in the test region 114. As explained below in more detail, this can be used to diagnose a condition of the patient. The energy 120 can be any form of energy that causes heating of test region 114. Energy source 120 and sensor 122 may be housed in one unit. Alternatively, they may be housed separately.

In the embodiment depicted in the FIG. 1 inset, the analyte binding molecules and capture molecules are shown to be monoclonal antibodies. The analyte binding molecule and the capture molecules may be the same type of molecule, i.e. an antibody. In such instances, they preferably bind the analyte at different sites, in other words, the analyte binding molecule and the capture molecule preferably do not bind to the same site or epitope of the analyte. Alternatively, the analyte binding molecule and the capture molecule can be two different molecules, but both capable of binding the analyte at different sites.

In the exemplary embodiment discussed above, antibody-coated GNPs are moved within a nitrocellulose strip through capillary action after the strip has been dipped or contacted with a clinical specimen. When present, the target antigen binds to monoclonal antibody-coated GNPs. This bound complex stops wicking up the "dipstick" when captured by an antibody on the membrane that recognizes the antigen-antibody-GNP complex. This leads to accumulation of GNPs at the test region 114 of the LFA, creating a positive test result. GNPs have been used for LFAs because their size can be designed to migrate through the pores of the membrane 112; GNPs can be coated with antibodies easily; and GNPs have a strong interaction with visible light thus producing deep color that is easily visualized. GNPs that have strong interaction with light at other light wavelengths may be used for thermal contrast detection, for instance gold nanorod with maximum light absorption in the near infrared.

Figure 2A:
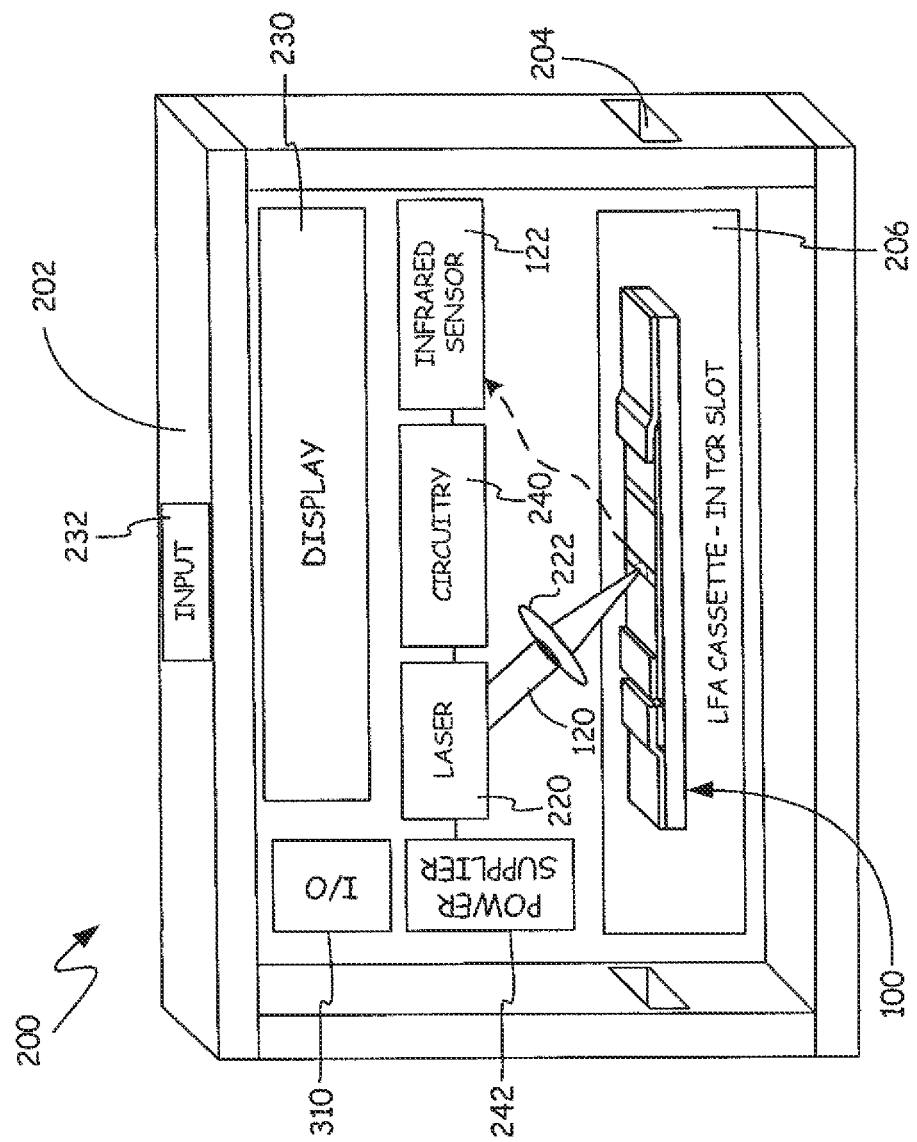
FIG. 2A is a simplified block diagram of a portable assay reader.

FIG. 2A is a simplified block diagram of a portable assay reader 200 in accordance with one example embodiment of the present invention. Reader 200 includes a housing 202 having an opening 204 therein configured to receive the LFA 100 in a slot or holder 206. In FIG. 2A, a laser 220 generates energy 120 directed to the test region of the LFA 100. In FIG. 2A, the energy can be, for example, visible or near infrared light that is focused on the test region using an optional lens 222. As discussed herein, visible or near infrared light directed at nanoparticles can cause heating of the nanoparticles. This is detected with a sensor 122 such as an infrared sensor. The results of the test can be displayed on a display 230 which can comprise for example, LCD display. The display can provide a quantitative output or a qualitative output such as a simple pass/fail indication. An optional user input 232 is provided. For example, this input can be a single button allowing an operator to initialize a test, or can be a more complex input such as a numerical keypad or of a numeric keypad allowing an operator to update parameters such as threshold values used by the device 200. The input 232 can be an overlay on display 230 to provide a touchscreen.

Operation of device 200 is controlled by electronic circuitry 240 as described below in more detail. This may include, for example, a microprocessor, analog-to-digital converters, I/O circuitry, etc. A power source 242 is provided. Preferably, the power source 242 is a portable power source such as a battery or the like. The power source may optionally be rechargeable either through connection to another electrical source or using a solar cell or the like.

Additionally, device 200 includes input/output (I/O) circuitry 310 that is described below in more detail. I/O circuitry 310 allows data collected by the device 200 to be transmitted or otherwise provided to other devices. For example, test results can be collected and transmitted to a central location or cloud server for subsequent evaluation.

FIG. 2B is a simplified block diagram of assay reader 200 configured in a "bench top" configuration. In the configuration of FIG. 2B, a computer identified as PC is used to perform the testing. PC 260 couples to laser 220 and infrared sensor 122 through I/O circuitry 262. I/O circuitry 262 can include, for example, digital-to-analog converters, analog-to-digital converters, switchable outputs, etc. Typically, the PC 260 shown in FIG. 2B will have more computing power than that is available in a portable device. This may allow additional testing or more advanced testing to be performed.

Although any appropriate components may be employed, in one embodiment, the source 220 comprises a laser, for example a 532 nm green laser (i.e. LRS-0532-PFM_00200-03, LaserGlow Technologies Inc). Focusing optics 222 can comprise for example a plano-convext focusing lens. A suitable infrared sensor includes an infrared camera (A20 or E30, FLIR Inc) or infrared sensor (MLX90614, Melexis). However, the present invention is not limited to this configuration.

Figure 3:
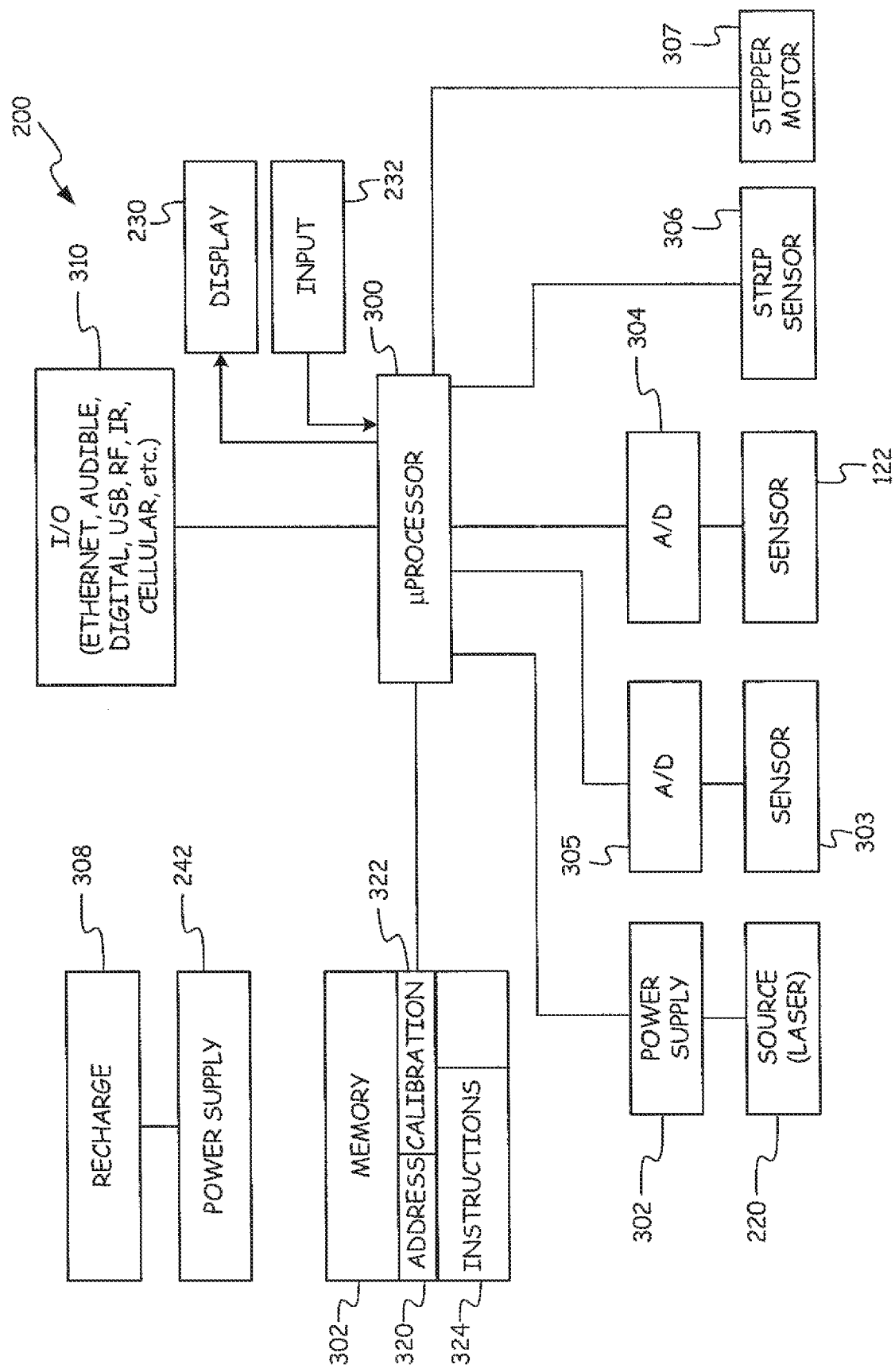
FIG. 3 is a simplified block diagram of the assay reader of FIG. 2A.

FIG. 3 is a simplified block diagram of device 200 and includes a microprocessor 300 operating in accordance with instructions stored in a memory 302. Microprocessor 300 controls the energy source 220 by activating energy source power supply 302. The heating of the LFA (not shown in FIG. 3) is detected by heat sensor 122 that provides an output to an analog-to-digital converter 304. An optional strip sensor 306 is provided. Strip sensor 306 can be configured to detect the presence of LFA 100 in slot 206 thereby allowing the microprocessor 300 to activate the energy source 220 and begin the test.

FIG. 3 shows an optional recharge circuit 308 connected to power supply 242. This may allow the power supply 242 to be recharged, for example, using an external power source, a solar cell, a mechanical crank, etc.

Input/output circuitry 310 is also illustrated coupled to microprocessor 300. This may include any type of input or output device including a display, keyboard or manual input, audible output, digital output such as a USB or Ethernet connection, an RF (radio frequency) or IR (infrared) input and/or output, a cellular data connection, an Ethernet connection, etc. Example RF connections include but are not limited to BLUETOOTH® connections or other short distance communication techniques, WIFI connections, or others. Cellular phone connections allow the device to communicate using a cellular phone network for communicating data and/or providing optional voice communication. The data may include the test results and geographic information (GPS location) to collect spatiotemporal information on infectious diseases.

The use of I/O 310 allows data collected by device 200 to be sent to another location. For example, when used in the field, device 200 can transmit test results back to a central database. This transmission can be through any appropriate technique. For example, data can be sent through an Internet connection, over a cellular network, etc. The connection may require a physical wired connection or may occur wirelessly using WIFI, Bluetooth, etc. Additionally, the I/O can be used to update information stored in the memory 302. For example, programming instructions, calibration information or other data may be updated. The I/O 310 may also be used to communicate with an operator from a remote location using display 230 and/or input 232.

During operation, a LFA 100 (not shown in FIG. 3) is placed within housing 202, for example through slot 204 (shown in FIG. 2). The test process is initiated by microprocessor 300 in response to a signal from the strip sensor 306, or some other trigger such as a manual input using input/output circuitry 310. In one configuration, an optional stepper motor 307 is provided and controlled by the microprocessor 300. The stepper motor 307 can be used to automate the movement of the LFA 100 within the device 200. The multiple strip sensors 306, or other configurations can be used if it is desired to monitor the location of the LFA 100 within the device 200. This causes the microprocessor 300 to apply power to the energy source 220 thereby heating the LFA 100. The heating response is sensed by sensor 122 and converted into a digital signal using an analog-to-digital signal converter 304. Based upon this digitized signal, the microprocessor 300 provides an output using input/output circuitry 310 that is indicative of the test results.

Additionally, FIG. 3 shows a feedback sensor 303 that is arranged in the path of source 220 in order to sense the strength of the applied energy. The output from the feedback sensor 303 is provided to the processor 300 through an analog to digital converter 305. For example, sensor 303 can be a light sensor to sense the intensity of the output from a laser 220. This information can be used to calibrate operation of the device and calibrate the sensed heating. Further, the feedback can be used for diagnostic purposes in order to detect a source 220 that is putting out a weak signal or has failed completely.

Memory 302 is used by microprocessor for short and long-term storage of information. For example, addressing information 320 of the device 200 can be stored in memory 302. This address may be, for example, an address that uniquely or semi-uniquely identifies the device 200 and may include, but is not limited to an Internet protocol (IP)

address, a Mac address, or other address format. The memory 302 may also be used to store calibration information that can be used to calibrate the data received from sensor 122. The calibration information can be determined in any number of ways including, for example, during manufacture of the device, input using circuitry 310, or based upon a calibration performed using a LFA 100, for example, using calibration region 116 shown in FIG. 1. This calibration information can provide a baseline or other type of offset to the readings provided by the sensor 122. Memory 302 also includes operating instructions 324 which are used to control operation of the microprocessor 300.

FIGS. 4A and 4B are graphs which illustrate the heating response of LFA 100 when energy 120 is applied, $T_S$. The amount of heating reaches a maximum indicated by $R_M$. Further, as illustrated in FIGS. 4A and 4B, the response has a slope which begins at its steepest rise and slowly levels off to the maximum level $R_M$. Microprocessor 300 operates as diagnostic circuitry by analyzing the heating response to the applied energy signal. For example, a simple threshold level can be used in which the maximum response is compared to a threshold level. This can be provided as an output, for example a "pass/fail" output based upon the comparison. Further, a quantitative output can be provided based upon the maximum response level. This quantitative output can illustrate the amount of gold nanoparticles that have been captured at the test location 114 (shown in FIG. 1). This can be correlated to, for example, the amount of antigen and therefore the progression of a disease in the patient.

In one aspect of the present invention, the diagnostics are based upon the profile of the response. For example, in FIGS. 4A and 4B, an initial slope of the response is illustrated. Based upon this initial slope, it is possible to extrapolate the value of $R_M$ without the necessity of allowing the heating to reach the maximum value. This technique can be used to increase the speed of the testing process. Further, this information can also be used to verify the value of $R_M$ detected by the sensor 122. For example, if the extrapolated value of $R_M$ differs significantly from the measured value of $R_M$, it may be an indication of a failing component, a damaged test strip, or some other error in the measurement. Further, as discussed above, the calibration information can be used to improve the accuracy of the measurements. For example, the calibration information can provide a baseline response to which the response signal is compared. Thus, the response threshold levels can be adjusted based upon the calibration information.

The energy source 220 can be any appropriate energy source. In one embodiment, the energy source 220 comprises a laser. A variety of lasers are known in the art for use as a heat source and can be, for example, a continuous wave laser, pulsed wave laser or a reduced size laser. Thermal contrast sensitivity may be increased by using higher powered lasers and/or tuning the laser power for different concentrations of GNPs to extend the dynamic range. The laser can emit light in the visible range. Lasers may also be used that emit light in the near infrared region. Generally, the laser is selected and tuned to maximize the absorption within the nanoparticles while minimizing the interference from the background materials. The amount of laser power used in the LFA system can vary and is dependent on the components of the assay. In an exemplary embodiment, the laser power was between about 5 W and about 50 W (continuous wave laser). However, higher or lower energy levels may be used in other embodiments. For instance, lower total energy but higher energy density may be applied with pulsed laser. With the reduction of background absorption discussed below, higher laser power maybe used for further improved sensitivity and signal strength.

Generally, the membrane, and backing include materials that have minimal light absorption. Background heating limits the ability to use higher energy to obtain higher signal strength. By selecting materials that have minimal light absorption, the background thermal reading can be reduced to ensure that the thermal detection is from the nanoparticles in the test region and not the materials of the assay system. The membrane in the LFA system is generally a porous material containing a plurality of interstices or pores. Liquid can flow through these interstices or pores generally by capillary action. The porous material can be made from natural or synthetic substances. Suitable porous materials for use in the LFA systems can include, for example, nitrocellulose, polyvinylidene fluoride (PVDF), polyethylene, nylon, cellulose acetate, polyester, polyethersulfone (PES), polysulfone and the like. In one embodiment, membrane that has the smallest light absorption is used. Other porous materials may also be used that are known in the art. A variety of backings are known in the art and mainly provide structural support for LFA. For thermal contrast detection, materials that have minimal light absorption can be used as backing in the LFAs described herein. In one embodiment, the backing can be made of glass or plastic (for instance polystyrene). Sample pad can be made from a variety of materials including, for example, polyester, polyacrylic, other polymeric materials or glass fiber. Conjugate pad and absorbent pad can be made from, for example, cellulosic materials or the like.

Metallic nanoparticles generate heat upon optical stimulation. This heat generation results from surface plasmons at the metal-dielectric interface during transition from an excited to ground state. The amount of heat generated by GNPs, for example, can be described by the following equation:

$$Q = NQ_{nano} = NC_{abs}I \qquad \text{Equation (1)}$$

where the total heat generation (Q, W/m³) is the combined contribution of single GNP ($Q_{nano}$), written as the product of GNPs concentration (N, #/m³), GNP absorption cross section (m²), and laser intensity (W/m²).

The nanoparticles that can be used in the assays described herein can include a variety of materials, shapes and sizes. The nanoparticles can be gold nanoparticles, silver nanoparticles, carbon nanoparticles, copper nanoparticles, platinum nanoparticles, aluminum nanoparticles, cadmium nanoparticles, composite particles, i.e. silver and gold, graphene nanoparticles and the like. In one embodiment, the LFA assay system includes gold nanoparticles. Other types of nanoparticles may also be employed and are within the scope of this description. Some embodiments are described herein using gold nanoparticles but it is understood that other nanoparticles may also be used and the embodiments are not limited to gold nanoparticles. In alternative embodiments, a combination of two or more types of nanoparticles may be used. These may be used to identify multiple analytes or to amplify or enhance the signal.

The nanoparticles can include a range of sizes and generally must be able to travel through the membrane. The diameter of the nanoparticles can be in a range from about 10 nm to about 400 nm. In one embodiment, the diameter of the nanoparticles can be in a range from about 20 nm to about 400 nm. In one exemplary embodiment, gold nanoparticles, e.g. gold nanospheres, of about 100 nm in diameter are used. In another exemplary embodiment, gold nanoshells of about 150 nm are used. In one exemplary embodiment, gold nanorods are used. In another exemplary embodiment, gold nanospheres of about 150 nm diameters are used.

The selection and optimization of nanoparticle size depends partly on the energy absorption. For one embodiment with laser as the energy source and gold nanoparticles, the physical phenomenon named plasmon resonance enhances the efficiency of optical absorption and therefore heat generation. Larger sizes are available and may also be used and are included in the scope of the present description. In some embodiments, GNPs with sizes of about 40-80 nm have the higher absorption efficiency (defined as $Q_{abs}=C_{abs}/A$, where Cabs is the absorption cross section and A is the projected cross sectional area of the particle) and can be used from heat generation point of view.

The selection and optimization of the nanoparticle size can also be determined by the binding affinity of the nanoparticles coated with the analyte binding molecules to the analyte. The binding affinity, in turn, can be determined by the size of the nanoparticles. Larger nanoparticles can be loaded with higher amounts of analyte binding molecules and thus, can have greater affinity to the analyte. Larger size GNPs can have stronger light absorption and scattering properties thus improving GNP detection. The upper limit of the size of the nanoparticles can be determined by the size of the pores in the membrane of the assay system since the nanoparticles coated with the analyte binding molecules would have to be small enough to diffuse through the pores in the membrane. The nanoparticle size has little effect on the convective velocity. Hence the Pe ($=UR/D_e$) is still <<1 and diffusion is rate limiting for GNP transport as GNP size increases.

A variety of shapes of nanoparticles can be used in the LFA system described herein and all are within the scope of the invention. The nanoparticles can be, for example, nanospheres, nanorods, nanoshells, nanocubes, nanourchins, nanopyramids, nanostars, and the like. In some embodiments, the nanoparticles are nanospheres, nanorods, nanoshells, (silica core-gold shell nanoparticles, magnetic core-gold shell nanoparticles and other core-shell nanoparticles), nanohorns, nanocubes, nanourchins, nanoflowers, nanoparticles with other plasmonic configurations and combinations thereof. Any of these shapes of nanoparticles with the materials described herein can be used. The nanoparticles with the highest optical absorption efficiency and that can be functional in the assay with regards to other properties are preferable. For particles with nonspherical shape, effective radius (sphere with equivalent volume) may be used to calculate the absorption efficiency.

The polydispersity of the GNPs used in existing LFAs are not well controlled, as seen in FIGS. 12A-C and 13 for CrAg and hCG dipsticks. Better control of polydispersity leads to more uniform nanoparticles size distribution. This can lead to smaller standard deviations for thermal contrast detection, and therefore improves the signal stability and consistency. More uniform nanoparticles may also give higher optical absorption and heat generation. For instance, GNPs with different sizes have peak absorption at different wavelengths. For polydispersed GNP population, less GNPs will generate heat at peak absorption wavelength and thus reducing the amount of heat generated. In a sample of nanoparticles, well-dispersed nanoparticles of uniform size are preferable to nanoparticle clusters. Clustering of the nanoparticles can lead to less uniform absorption by the nanoparticles. The nanoparticles may, optionally, be coated to decrease clustering thereby increasing uniformity of absorption. The coating, if present, preferably does not reduce the absorption within the nanoparticles.

The size distribution of the nanoparticles can vary. In some embodiments, at least about 60 percent of the nanoparticles are within +/−10 nm of the mean diameter of the nanoparticles. Preferably, at least about 70 percent of the nanoparticles are within about +/−5 nm of the mean diameter of the nanoparticles. More preferably, at least about 70 percent of the nanoparticles are within about +/−3 nm of the mean diameter of the nanoparticles. Even more preferably, at least about 75 percent of the nanoparticles are within about +/−3 nm of the mean diameter of the nanoparticles. Nanoparticles outside of these ranges are also within the scope of the invention.

The amount or concentration of nanoparticles used in an LFA system can vary depending on the specific assay, the specific nanoparticles, the analyte binding molecules and the like. Generally, the amount of nanoparticles can be on the order of about 1-1000 μg. Nanoparticle amounts outside of this range may also be used and are within the scope of this invention. For one embodiment, CrAg assay uses about 4 μg of GNPs per LFA. The amount of nanoparticles used can be higher or lower than the specified range depending on binding affinity of the binding molecules, concentration range of target analyte in the patient samples, among other factors.

Figure 15A:
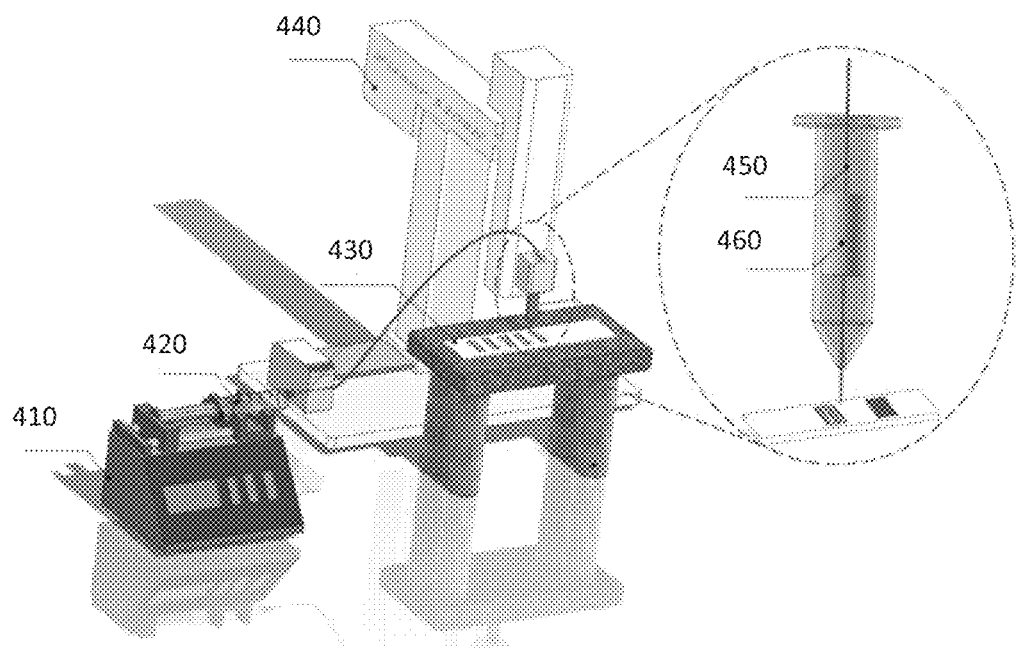
FIG. 15A is a diagram of one embodiment of a system used for printing GNPs onto a membrane using 3D printer.

The present description can also include a method of printing gold nanoparticles uniformly, quantitatively and without aggregation onto nitrocellulose membrane. This can be used to quantitatively compare the visual and thermal signal of different size and shape gold nanoparticles, therefore assisting in the optimization of gold nanoparticle in LFA. FIG. 15A is a diagram of one exemplary embodiment of a system that can be used for printing GNPs onto a LFA membrane. Other printing systems may be used and are within the scope of this description. The printing, for example, can be performed using a 3D printer 440. Briefly, syringe pump 410 can include syringe 420. 3D-printer 440 can be used to print on membrane 430. The gold nanoparticle solution (gold nanoparticles suspended in 65% w/w glycerol) flows from syringe 420 to capillary tube 450 surrounded by rubber 460. The gold nanoparticle solution in syringe 420 can be printed onto LFA membrane using syringe pump 410 to control the amount of gold nanoparticle printed and 3D printer 440 to control the uniformity of printed gold nanoparticles.

Analytes in a variety of samples may be determined and generally can be any type of liquid sample. The samples may be biological samples, chemical samples, environmental samples, food samples and the like. Biological samples can include, for example, blood, plasma, serum, urine, stool, sweat, bile, cerebrospinal fluid, fecal material, vaginal fluids, saliva and the like. Other biological samples may also be analyzed and are all within the scope of this invention. The sample with the analyte may be used directly or diluted using diluent. Diluent can be a variety of solutions and are generally known in the art. In an exemplary embodiment, the diluent is a saline solution.

A variety of analytes can be detected using the methods and devices of the present description. A target analyte can be a protein, peptide, nucleic acid, hapten, chemical and the like. Analytes can also include therapeutic drugs, drugs of abuse, hormones, vitamins, glucose proteins, antibodies, steroids, bacteria or bacterial infection, fungi, viruses, parasites, components and products of bacteria, allergens, antigens and the like. An analyte can also include derivatives or metabolites of the compound of interest.

In some embodiments, the analyte can be associated with a disease, for example, malaria, TB and the like. In other embodiments, the analyte can be associated with a physiological or pathological condition, for example, pregnancy. Examples of analytes include Cryptococcal antigen (CrAg), malarial antigen, Tuberculosis antigen, human chorionic gonadotropin (hCG), human luteinizing hormone (hLH), human follicle stimulating hormone (hFSF), prostate specific antigen (PSA), hepatitis B surface antigen, hepatitis B antibodies, HIV antigen, *Streptococcus* A, *Staphylococcus* bacteria, STDs, *P. Falciparum*, Fever panel and the like.

The analyte binding molecules and the capture molecules can be any molecule that is capable of binding the target analyte. In some embodiments, the analyte binding molecules and the capture molecules are biological macromolecules, for example, antibodies or parts of antibodies. These molecules can also be receptors, ligands, polynucleotides, polypeptides, glycopeptides, lipoproteins, nucleoproteins, nucleic acid, aptamer, and the like. In one exemplary embodiment, the analyte binding molecules and the capture molecules are antibodies. In some embodiments, the analyte binding molecules are the same as the capture molecules. In other embodiments, the analyte binding molecules are different than the capture molecules.

A variety of methods are known in the art to conjugate or couple the nanoparticles to the analyte binding molecules and all are within the scope of this invention. Generally, conjugation chemistry that allow improved stability at high temperatures, high or low humidities and/or radiative conditions are preferable. Chemical binding refers to the use of chemical functional groups and/or molecules that link the particles to the analyte binding molecule. An example is the placement of carboxylic acids on the surface of the particles to allow for linkage to amine functional groups on an antibody through a carbodiimide mediated molecule. Conjugation may involve passive adsorption. Passive adsorption is known in the art and disclosed, for example in US 2010/0136566 incorporated herein by reference.

A variety of liquid dispensing and spray technologies are known in the art for deposition of the capture molecules to the membrane. Any of these may be used and spray technologies that lead to better absorption and stability of the capture molecules are preferable. Nanoparticles conjugated to analyte binding molecules may also be sprayed onto the conjugate pad. In an exemplary embodiment, a variety of liquid dispensing instruments from BioDot™ may be used for these purposes.

The LFAs and methods of detecting analytes described herein can detect analytes across a broad range of analyte concentrations. The methods and assays described herein can be used to detect analytes at very low concentrations. In addition, the assays can also be used to detect analytes at high concentrations, e.g. beyond the hook effect. "Hook effect" as referred to herein relates to the phenomena which occurs at excessively high analyte concentrations, the amount of GNP captured at test region decreases with increasing analyte concentrations, leading to a decrease in test region signal.

The present description can include a method of detecting one or more analytes in a sample. The LFA analytical sensitivity can be substantially improved, potentially >10,000-fold over visual detection methods by the use of thermal contrast technology described herein.

The method can include contacting a sample with the sample pad and allowing the liquid to flow through the membrane by capillary action. Nanoparticles conjugated with the analyte binding molecules move within the membrane through capillary action in response to the sample application. When present, the target analyte binds to the conjugated nanoparticles. The nanoparticle/analyte complex stops moving though the membrane when the capture molecule in the test region recognizes and binds the nanoparticle/analyte complex. This leads to accumulation of the nanoparticle/analyte complex at the test zone or region of the LFA.

The method can further include using the thermal contrast reader to detect and quantitate the amount of analyte in the test region by first exposing the test region to an energy source such as a laser and then measuring the heat generated from the test strip by a sensor. The heat measured by the sensor can be correlated to the amount of analyte present in the test region of the test strip. The output generated by the sensor is indicative of the presence and/or amount of the target analyte. The method can also include detecting multiple analytes. Multiple analytes can be detected by having multiple test regions, wherein each test region has different capture molecules. Thus, the first nanoparticle/analyte complex binds to test region 1 having a first capture molecule that binds the first analyte, wherein the second nanoparticle/analyte complex binds to test region 2 having a second capture molecule that binds the second analyte and not the first analyte. In this manner, the LFA system can be extended to identify multiple analytes by configuring to include multiple test regions. Multiple analytes may also be detected using multiple nanoparticles having differing starting positions. The nanoparticles may have different conjugates and different analyte binding molecules. These can be tuned to have different flows through the membrane. The multiple analytes may be in the same sample or different samples. In some embodiments, multiple analytes may be tested in the same test region. The detection of the multiple analytes results in the identification, preferably with a quantitative amount of analyte, for each of the analytes in the corresponding test region. In some embodiments, the multiple analytes may also be detected and/or quantified cumulatively in one test region. For example, using different particles that absorb at different laser wavelengths allows multiplexing using laser excitation with corresponding wavelengths.

The method can also include amplification of the signals through the use of a secondary controlled flow of different nanoparticles. In one exemplary embodiment, the signal from a LFA with primary gold nanoparticles can be amplified by the use of silver staining or secondary binding nanoparticles. In the process of silver staining, the gold nanoparticles can act as a nucleation site for the growth of a silver shell on the surface. In the process of secondary nanoparticle binding, the secondary nanoparticle binds to the first particle that captures the target analyte to amplify the signal.

The present method also includes quantitation of the amount of analyte present in the test region. The measurement of the thermal change of the membrane can be correlated to the amount of analyte present in the test region. The LFA system can advantageously provide not only the presence or absence of analyte but also provides the level of analyte present in the membrane and consequently the sample. This is particularly advantageous for determining the extent of the disease, infection or condition in a patient.

After the test region is exposed to an energy source, the presence and amount of analyte can be detected by measuring the thermal change or temperature in the test region of the membrane. Alternatively, the initial rate of temperature change can also be measured to determine the specific absorption rate (SAR). SAR can be used to determine the amount of analyte present in the test region. SAR is in effect the Q in Equation 1 above. It relates to the amount of heat energy in W/m³ given off by the nanoparticles once they have been activated by an energy source such as a laser. As shown in Equation 1, it is directly proportional to the laser fluence and the number of nanoparticles which then relates directly to the amount of antigen in the analyte.

The LFAs described herein can be used in methods to detect analytes across a broad range of analyte concentrations. The assay can detect an analyte from about 3 $\log_{10}$ to about 6 $\log_{10}$. The range can be further expanded to about 7 $\log_{10}$. This can be accomplished, for example, by using higher laser power and/or low absorbing backing materials for the LFA. In one embodiment, the assay can detect an analyte over about 6 $\log_{10}$ concentration range. In one embodiment, C-reactive protein (CRP) can be detected over about 6 $\log_{10}$. In one embodiment, the range of the concentrations of the analyte detected using visual and thermal detection may be up to about 6 orders of magnitude (6 $\log_{10}$) or more. Each analyte will have its own range, but with thermal contrast assay, the range can be expanded.

The LFAs can be used in methods to detect analytes over a broad range of concentration by thermal detection of the analyte using the thermal contrast assay reader described herein. The LFAs may also detect analytes over a broad range of concentration by combining thermal detection and visual detection.

In one embodiment, the methods described herein using thermal detection can increase the sensitivity of the assay by at least about 100 fold relative to visual detection. In another embodiment, the methods described herein using thermal detection can increase the sensitivity of the assay by at least about 150 fold relative to visual detection. In one exemplary embodiment, the methods described herein using thermal detection can increase the sensitivity of the assay by at least about 200 fold or greater relative to visual detection. In another exemplary embodiment, the methods described herein using thermal detection can increase the sensitivity of the assay by at least about 1000 fold or greater relative to visual detection of 30 nm nanoparticles. In one exemplary embodiment, the methods described herein using thermal detection can increase the sensitivity of the assay by at least about 1600 fold or greater relative to visual detection of 30 nm nanoparticles.

The LFAs can be used in the methods described herein to detect analytes at very low concentrations. In one embodiment, LFAs can detect analytes at a concentration of about $10^{-4}$ mg/L or lower. Detection of analyte concentrations below these amounts are also within the scope of this description. The detection of analytes at these concentrations can include thermal contrast detection using a thermal contrast reader.

The methods and assays can be extended to detect analyte concentrations before and beyond the "hook effect". In some embodiments, the assays can include test regions that are test dots. Test dots can be used as test regions at a variety of analyte concentrations. In one embodiment, test dots and test dot patterns resulting after application of the sample can be used to determine the analyte concentrations in the sample before the "hook effect" and after the "hook effect".

In one embodiment, LFAs can detect analytes at a concentration of between about 19~38 mg/L. Detection of analyte concentrations above these amounts are also within the scope of this description. The detection of analytes at these concentrations can include thermal contrast detection using a thermal contrast reader.

Figure 17A:
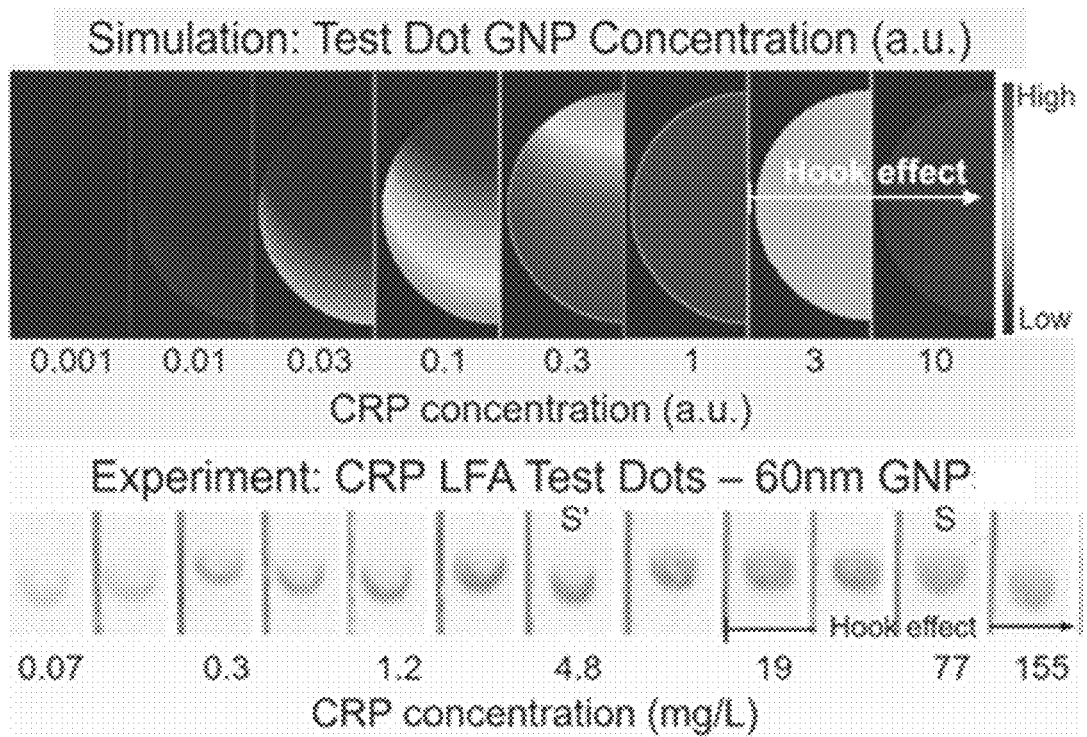
FIG. 17A is a schematic of modeling and experimental results of test dot visual reading and "hook" effect compensation.

In one embodiment, FIG. 17A illustrates a test dot pattern at various levels of analyte concentrations in a sample. In FIG. 17A, for analyte concentration <19 mg/L (before hook effect), as analyte concentration increase, the test dots are gradually filled from bottom to top (i.e., from partially filled bottom edges to fully filled dots); for analyte concentration >19 mg/L (after hook effect), as analyte concentration increases, the color intensity of the fully filled dots decreases.

In one embodiment, an LFA for detecting CRP can detect the CRP concentration in a sample of between about $10^{-5}$ mg/L to about 300 mg/L in one test. This range can be further expanded by using higher power laser and/or reducing the absorption in the background, e.g. transparent backing. In one embodiment, the LFAs can detect analyte concentrations from about 100s of micromolar (µM) down to about 100s of femtomolar (fM) concentration detection.

The present description can also include a method of enhancing or improving the analytical performance of LFAs. The method can include modeling that may be used to identify key parameters such as GNP size and concentration, reaction rate constant and flow speed that determine the analytical performance of LFAs. The method can include optimizing the size and/or shape of the nanoparticle to be included in the membrane based on the affinity of the analyte binding molecule to the nanoparticle and the diffusion and convection of the nanoparticle in a membrane of the LFA. The affinity of the nanoparticle coated with the analyte binding molecule to the analyte, e.g. $k_{on}'$, can vary. LFAs with higher binding affinity between the nanoparticles and the analytes can improve the analytical performance of a LFA, e.g. higher $k_{on}'$. The $k_{on}'$ can vary depending on, for example, type of assay, e.g. direct binding vs. sandwich assay. The $k_{on}'$ can also vary depending on the nanoparticles, analyte binding molecules and the analyte. The $k_{on}'$ can be at least about $10^3 M^{-1} s^{-1}$ to about $10^5 M^{-1} s^{-1}$ and $k_{on}'$ values higher than these can also improve the analytical performance. In some embodiments, a higher $k_{on}'$ is desirable since this is indicative of increased binding affinity between the nanoparticle and the analyte. In one embodiment, the $k_{on}'$ can be about $10^7 M^{-1} s^{31\ 1}$. In another embodiment, the $k_{on}'$ can be about $10^4 M^{-1} s^{-1}$. Other methods of enhancing the binding between the nanoparticles and the analyte are also within the scope of this description.

Aside from the improvement in the analytical sensitivity, the LFAs can also be archived for future analysis. Unlike other detection methods, there is no loss of signal using the thermal contrast system. In fluorescence measurements, organic fluorophores experience photobleaching. In some colorimetric measurements, the dyes may lose their signal over time through photodestruction. Thermal contrast readings conducted after two weeks of conducting the assay can be nearly identical. This advantageously allows for processing point-of-care LFAs in the field and referral to a central lab to process the same LFA system for thermal contrast readings. In other words, the analyte signal does not have to be measured immediately after the sample is run. The signal may be measured multiple times, for example, immediately after the assay is complete and also at a later time. The method can also include exposing the test region to the energy source and measuring the analyte in the test region after twelve hours, 24 hours or more after contacting the assay strip with the sample.

Cryptococcosis is among the leading causes of death among all AIDS-related opportunistic infections and is the most common cause of meningitis in adults in Africa causing >500,000 deaths worldwide annually. Cryptococcal meningitis is classically diagnosed by a combination of culture, India ink, or CrAg testing with semi-quantification by serial two-fold dilutions (i.e. CrAg titer, defined as the last positive test when performing two-fold serial dilutions).

The present description can include a method for detection and quantification of the CrAg antigen. The method includes contacting a sample with the sample pad and allowing the liquid to flow through the membrane by capillary action. Nanoparticles conjugated with the CrAg binding molecules move within the membrane through capillary action in response to the sample application. When present, the CrAg binds to the conjugated nanoparticles. The nanoparticle/CrAg complex stops moving though the membrane when the capture molecule in the test region recognizes and binds the nanoparticle/CrAg complex. This leads to accumulation of the nanoparticle/CrAg complex at the test region of the LFA. The thermal contrast system can be used to detect and quantitate the amount of CrAg in the test region by first exposing the test region to a heat source such as a laser and then measuring the heat generated from the test strip by a heat sensor.

Figure 6:
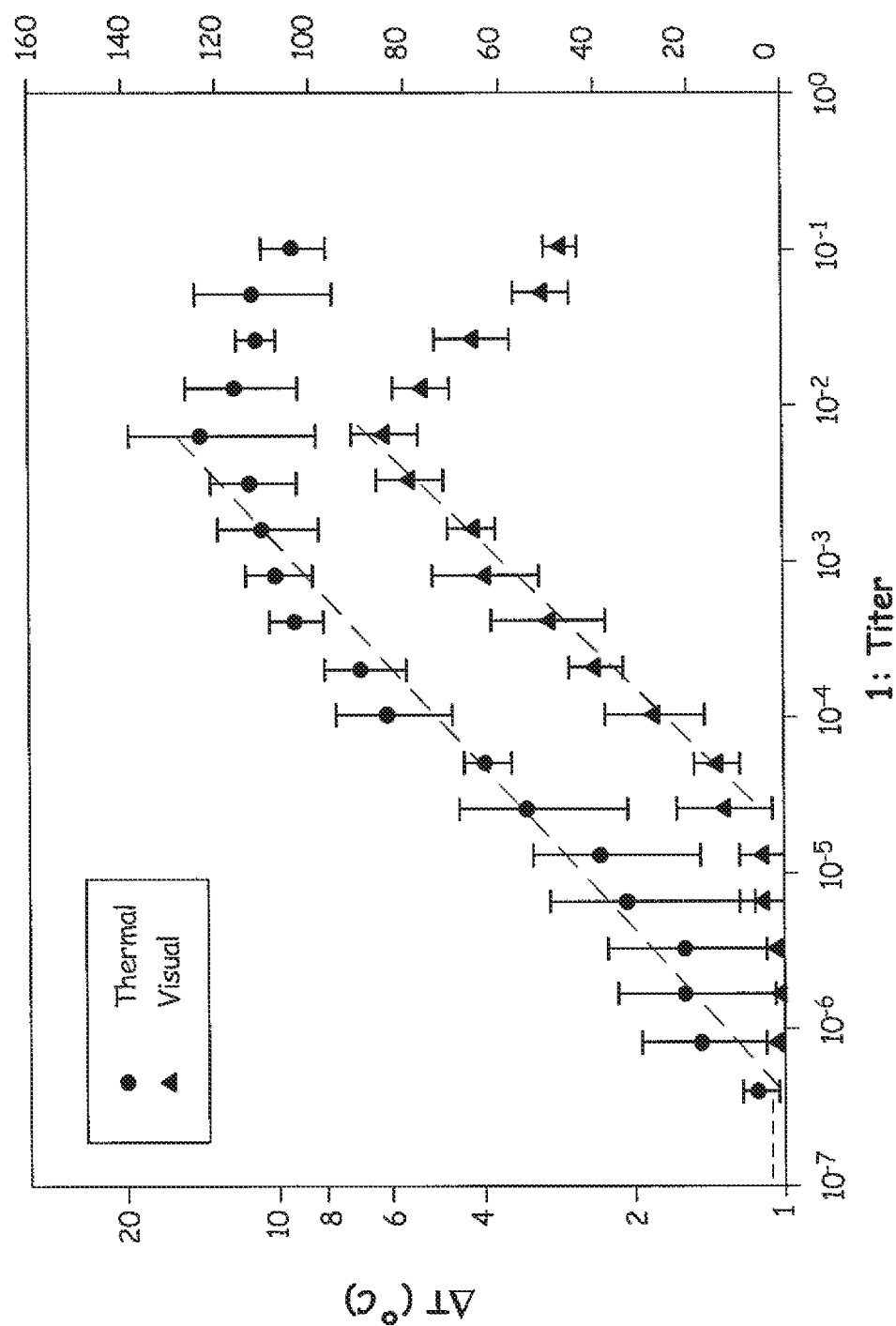
FIG. 6 is a graph that illustrates how thermal contrast enhances the detection of existing immunochromatographic lateral flow assays for cryptococcal antigen (CrAg). The plateau of signal at high concentrations is due to the high dose hook effect of the LFA. The dashed line shows background from the control sample.

FIG. 6 shows thermal contrast produced a 32-fold greater improvement in the analytical sensitivity than colorimetric detection with a log-linear slope up to an equivalent concentration of 1:1024 CrAg titer by latex agglutination ($R^2$=0.98). Above this 1:1024 titer, there was a high dose "hook" effect with decreased visual intensity and a plateau of thermal intensity. This can be overcome either by changing the dilution of the assay, or changing the engineering of the assay. In addition, the inter-assay precision of the assay can be improved by standardizing the size of these nanoparticles to decrease the coefficient of variance. For comparison, the median CrAg titer observed in patients with cryptococcal meningitis is often 1:1024 to 1:2048. However, there is a sub-acute onset over weeks to months with CrAg titers >1:8 in asymptomatic persons with subclinical disease predictive of later development of cryptococcal meningitis with 100% sensitivity and 96% specificity despite HIV therapy. Serum CrAg screening and preemptive antifungal treatment in persons living with advanced AIDS aborts the clinical progression to symptomatic meningitis. Non-invasive screening is possible with CrAg being detectable in urine, but urine has 22-fold lower CrAg concentration than blood. Thus, improvement in LFA sensitivity by thermal contrast can enable non-invasive screening of asymptomatic persons with AIDS, and the ability to quantify CrAg burden to risk stratify.

The present description can include a method for detection and quantification of the hCG antigen. The method can include contacting a sample with the sample pad and allowing the liquid to flow through the membrane by capillary action. Nanoparticles conjugated with the hCG binding molecules move within the membrane through capillary action in response to the sample application. When present, the hCG can bind to the conjugated nanoparticles. The nanoparticle/hCG complex stops moving though the membrane when the capture molecule in the test region recognizes and binds the nanoparticle/hCG complex. This can lead to accumulation of the nanoparticle/hCG complex at the test region of the LFA. The thermal contrast system can be used to detect and quantitate the amount of hCG in the test region by first exposing the test region to a heat source such as a laser and then measuring the heat generated from the test strip by a heat sensor.

The present description can include a method for detection and quantification of the malaria antigen. The method includes contacting a sample with the sample pad and allowing the liquid to flow through the membrane by capillary action. Nanoparticles conjugated with the malaria antigen binding molecules move within the membrane through capillary action in response to the sample application. When present, the malaria antigen binds to the conjugated nanoparticles. The nanoparticle/malaria antigen complex stops moving though the membrane when the capture molecule in the test region recognize and bind the nanoparticle/malaria antigen complex. This leads to accumulation of the nanoparticle/malaria antigen complex at the test region of the LFA. The thermal contrast system can be used to detect and quantitate the amount of malaria antigen in the test region by first exposing the test region to a heat source such as a laser and then measuring the heat generated from the test strip by a heat sensor.

The present description can include a method for detection and quantification of the TB antigen. The method includes contacting a sample with the sample pad and allowing the liquid to flow through the membrane by capillary action. Nanoparticles conjugated with the TB antigen binding molecules move within the membrane through capillary action in response to the sample application. When present, the TB antigen binds to the conjugated nanoparticles. The nanoparticle/TB antigen complex stops moving though the membrane when the capture molecule in the test region recognizes and binds the nanoparticle/TB antigen complex. This leads to accumulation of the nanoparticle/TB antigen complex at the test region of the LFA. The thermal contrast system can be used to detect and quantitate the amount of TB antigen in the test region by first exposing the test region to a heat source such as a laser and then measuring the heat generated from the test strip by a heat sensor.

EXAMPLES

Example 1—Synthesis and Analysis of GNPs

Gold nanoparticle (GNP) synthesis: 30 nm GNPs were synthesized by citrate reduction of chloroauric acid and then coated with polyethylene glycol (PEG) to maintain stability in aqueous solutions as described in Frens Nat. Phys. Sci. 1973; Perrault et al. Nano Letters 2009 9 (5) 1909-1915; Shah et al. Molecular Pharmaceutics 2012 9 (8) 2146-2155. Characterizations of GNPs by UV-Vis spectrophotometer, atomic emission spectroscopy, dynamic light scattering and TEM were performed to ensure the success of the synthesis and quantify concentration and size. Titrated concentrations of GNP water solutions were prepared and 10 µL of each solution was transferred to a glass slide as a drop. Laser beam from a CW Laser (532 nm, Millennia Vs, Diode pumped) then irradiated the drop for 1 minute, thereby inducing GNP heat generation. An infrared camera (FLIR ThermoVision™ A20) mounted at an angle above the sample measured temperature change remotely during laser irradiation. The maximum temperature change for each sample was determined from the thermal images and plotted.

The thermal contrast versus visual contrast of GNPs in solution was compared. A series of different concentrations of GNPs were prepared. 10 µL of the GNP solution was placed on a microscope slide. For visual analysis, a picture was taken by a digital camera and analyzed later with Image J. For thermal analysis, the GNP solution was irradiated with laser (0.5 W, 532 nm) and the temperature change was recorded by an infrared camera.

The results showed that GNPs can be detected down to $2.5 \times 10^9$ nanoparticles/mL of GNPs using thermal contrast in comparison to $2.5 \times 10^{11}$ nanoparticles/mL by visual contrast.

Figure 5:
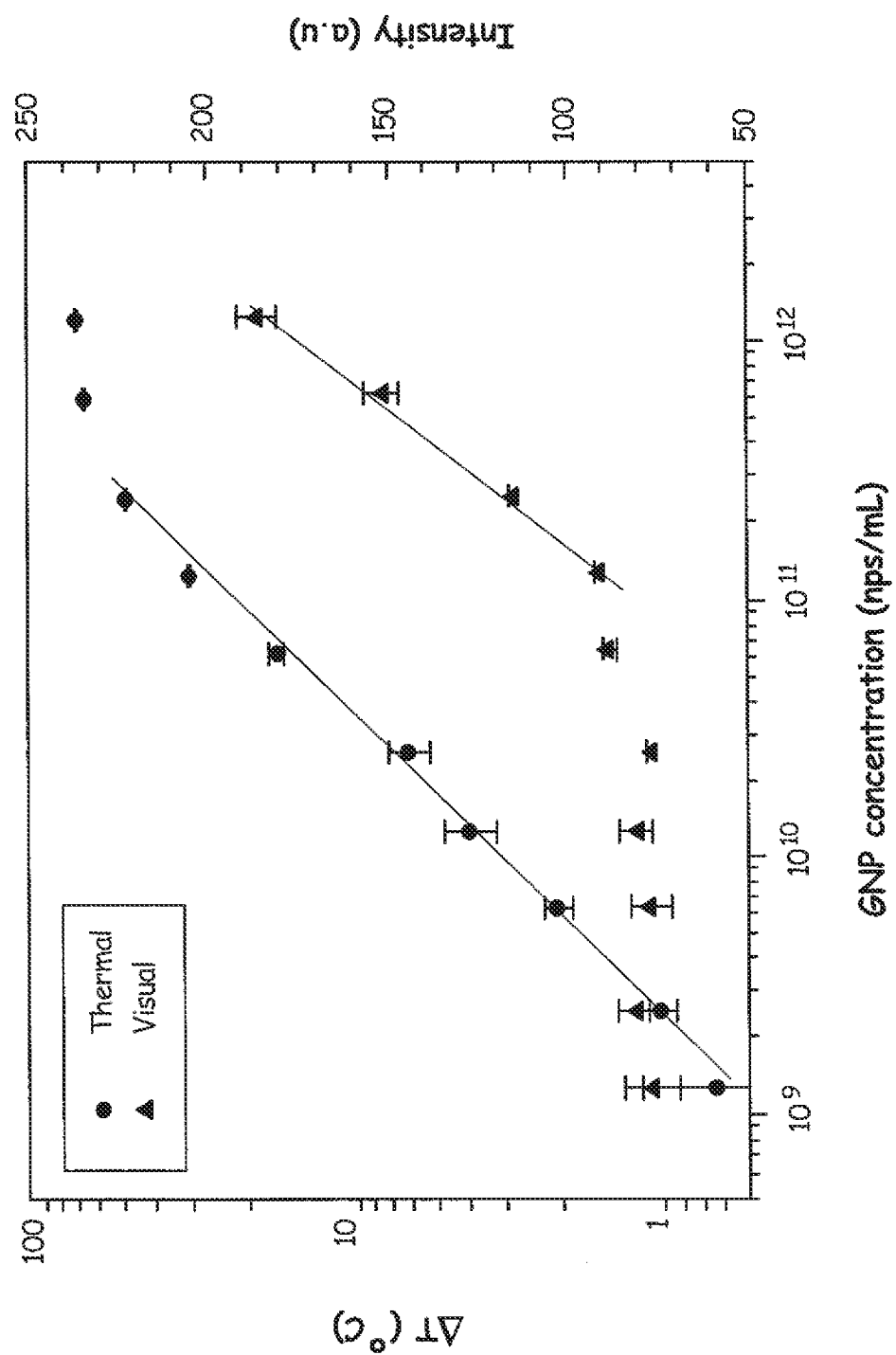
FIG. 5 is a graph illustrating the use of gold nanoparticles (GNPs) in a thermal contrast assay.

This clearly demonstrated that thermal contrast for detection can improve the overall analytical sensitivity by 100-fold (FIG. 5). The thermal contrast of GNPs was also compared with standard optical density measurement using a standard micro-volume plate reader, the principle of which is widely used in microfluidic ELISA. With the same sample volume (10 µL), the thermal contrast displayed 50-fold improvement over the optical density measurement. Further improvement in thermal contrast sensitivity can be possible by using higher powered lasers and/or tuning the laser power for different concentrations of GNPs to extend the dynamic range of thermal contrast. Importantly, by tuning laser wavelength to a higher absorbing nanoparticle (gold nanorod) we may also be able to increase the sensitivity.

Example 2—Detection of the Cryptococcal Antigen(CrAg)

The analytical performance of thermal contrast versus colorimetric detection (i.e. visual contrast) was tested using FDA-approved LFAs for detecting cryptococcal antigen (CrAg) obtained from Immy, Inc. and described in Qin et al. Angewandte Chemie 2012. Thermal contrast imaging of LFAs: Cryptococcal antigen LFA (Immy, Inc. Norman, Okla.), which was FDA-approved in July 2011, detects the capsular polysaccharide antigens of *Cryptococcus* species complex (*Cryptococcus neoformans* and *Cryptococcus gattii*) in serum and cerebrospinal fluid (CSF). A serum sample from a patient with cryptococcal meningitis had 2-fold serial dilutions performed to assess the limits of detection, as the CrAg titer. The test was conducted following the manufacturer's instructions. Thermal contrast was performed by irradiating the test line by laser for 1 minute. An infrared camera recorded temperature change. Three spots on each horizontal test band were irradiated and the average maximum temperature change was measured. At each concentration, three separate LFA dipsticks were run. The results are shown in FIG. 6.

Visual contrast quantification: For the GNP droplets, images were taken by a digital camera. The dipsticks were scanned by a flatbed scanner (Model: Visioneer Onetouch 7400). The mean grey intensity for regions of interest (ROI). i.e. droplet and the test band for dipsticks, was analyzed. The same volume of GNP solution (10 µL) was also measured by a spectrophotometer at 530 nm, with a Take3 micro-volume plate and Synergy HT Multi-Mode Microplate Reader (BioTek, Winooski, Vt.).

The LFA serial 2-fold dilutions of a serum sample, positive at 1:32768 titer by latex agglutination (Immy, Inc.) were compared. Results showed that thermal contrast was indeed more sensitive than colorimetric visual detection on the LFA. FIG. 6 shows thermal contrast produced a 32-fold greater improvement in the analytical sensitivity than colorimetric detection with a log-linear slope up to an equivalent concentration of 1:1024 CrAg titer. Above this 1:1024 titer, there was a high dose "hook" effect with decreased visual intensity and a plateau of thermal intensity.

Using FDA-approved cryptococcal antigen (CrAg) LFAs, a 32-fold improvement in analytical sensitivity with thermal contrast was seen (FIG. 6) while simultaneously quantifying the antigen concentration. This enhanced sensitivity in a "disposable RDT with a reader" model can enable CrAg screening and quantification in resource-limited areas for both symptomatic and asymptomatic CrAg+allowing targeted preemptive antifungal therapy in patients previously undetected by the qualitative LFAs.

Example 3—Improving Analytical Sensitivity of LFAs

Figure 7A:
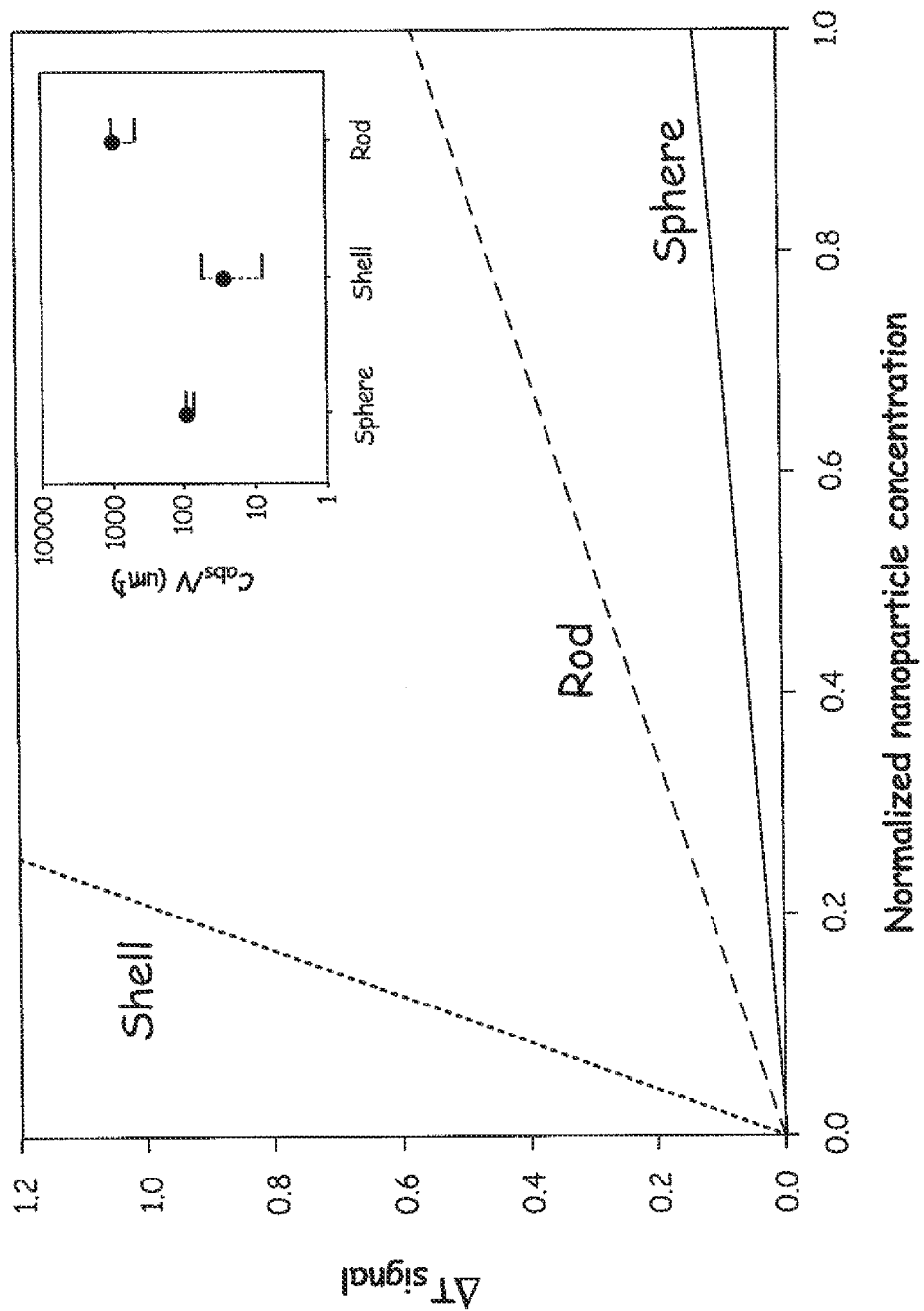
FIG. 7A is a graph of nanoparticle concentration versus temperature change for different nanoparticle shapes.
Figure 7B:
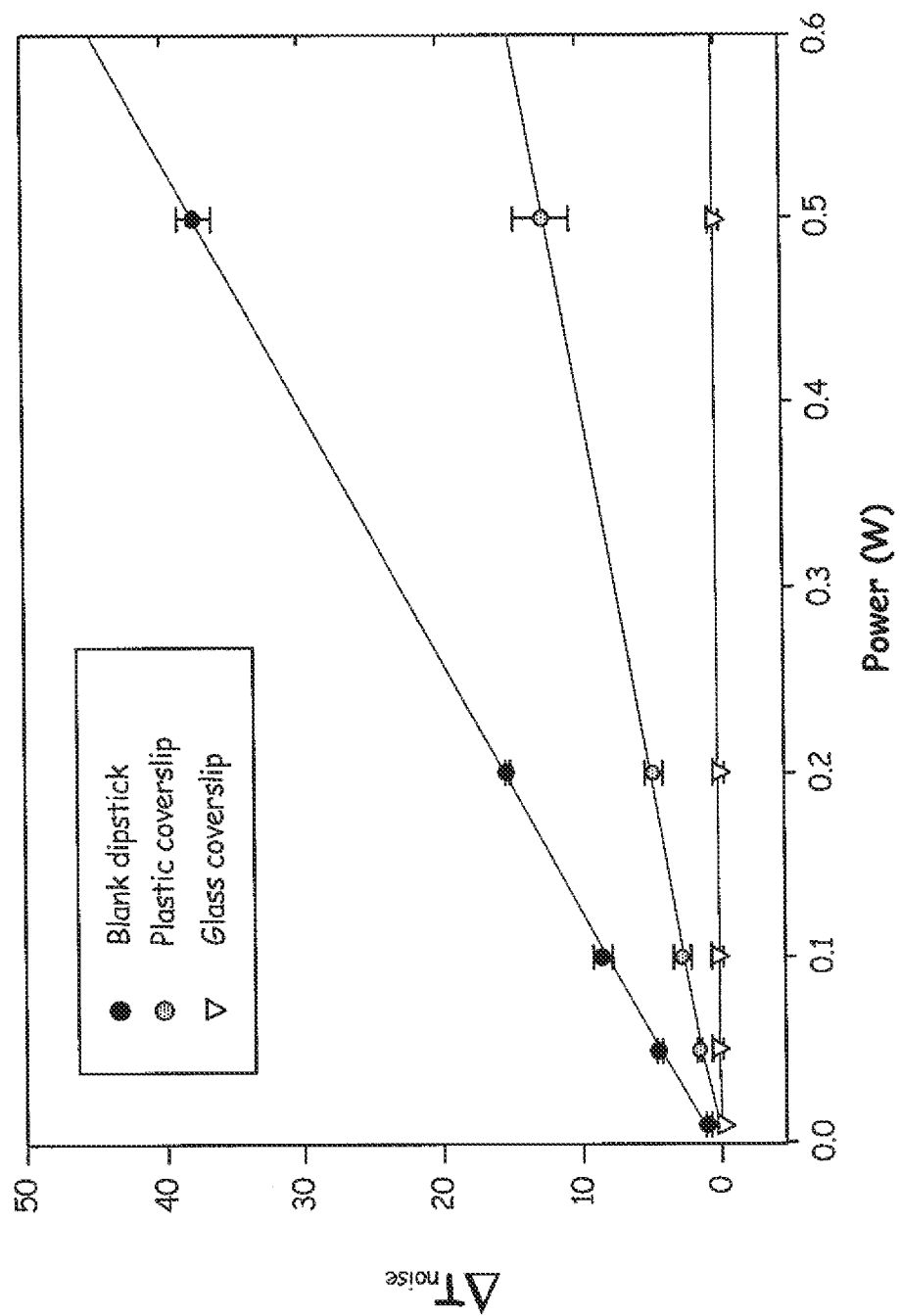
FIG. 7B is a graph of temperature change for different materials.

Modeling was conducted based on experimentally measured absorption cross sections of a variety of gold nanoparticles such as rods, shells and spheres to explore further improvement of the analytical sensitivity of LFAs. Gold nanoparticles including gold nanorods, nanoshells, and gold nanospheres were evaluated. As shown in FIG. 7A, at the equivalent laser power and nanoparticle concentration, typical nanorods and nanoshells generate 4.6-fold and 36-fold more heat than gold nanospheres, respectively. To eliminate the particle size effect, the absorption cross section ($C_{abs}$) was normalized by particle volume (V) to give a better assessment of the heat generation capability. The sizes of the GNPs used for this comparison were: sphere D=30 nm, nanorod D=12.7 nm by L=49.5 nm, and nanoshell $D_{core}$=120 nm (silica), $D_{shell}$=150 nm (gold). The thermal contrast ($\Delta T_{signal}$) and nanoparticle concentrations are normalized. Using this normalization, gold nanorods were about one order of magnitude more efficient in heat generation than the gold nanospheres and nanoshells (FIG. 7A inset). In addition, current LFAs (i.e. thin nitrocellulose membranes with thick backing material) absorb significant amounts of laser energy (at 532 nm) creating background heating or noise. Thus, use of low absorbing (i.e. high transmitting or reflective) backing materials, such as plastic or glass, allows the use of higher laser intensities (I). Substrate absorption: A blank dipstick and plastic and glass cover glasses were irradiated with 532 nm laser for 1 minute each. The temperature change during laser irradiation was measured by infrared camera and the maximum temperature change determined. (See FIG. 7B) Combining higher absorbing nanoparticles and low absorbing LFA backing materials can increase the sensitivity. It is worth noting that the gold nanorod may absorb efficiently at different wavelength than the gold nanosphere.

A 1000-fold further increase in thermal contrast can be produced by increasing the power density by 100 times (i.e., increase in laser power from 0.01 to 1 W) and using a nanoparticle with a 10-fold increase in absorption ($C_{abs}$). Higher laser powers can be used by reducing background absorption discussed above.

The analytical sensitivity of the assays can be improved by about 10,000 fold, considering the over 10 fold improvement shown and 1000 fold improvement predicted above over visual detection methods using the modifications described here.

Example 4—Detection of hCG

The presence of hCG (pregnancy test) in a sample was tested using a LFA with the GNPs. The hCG LFA was purchased from Fisher Scientific (Sure-Vue Serum/Urine hCG test kit).

Figure 8A:
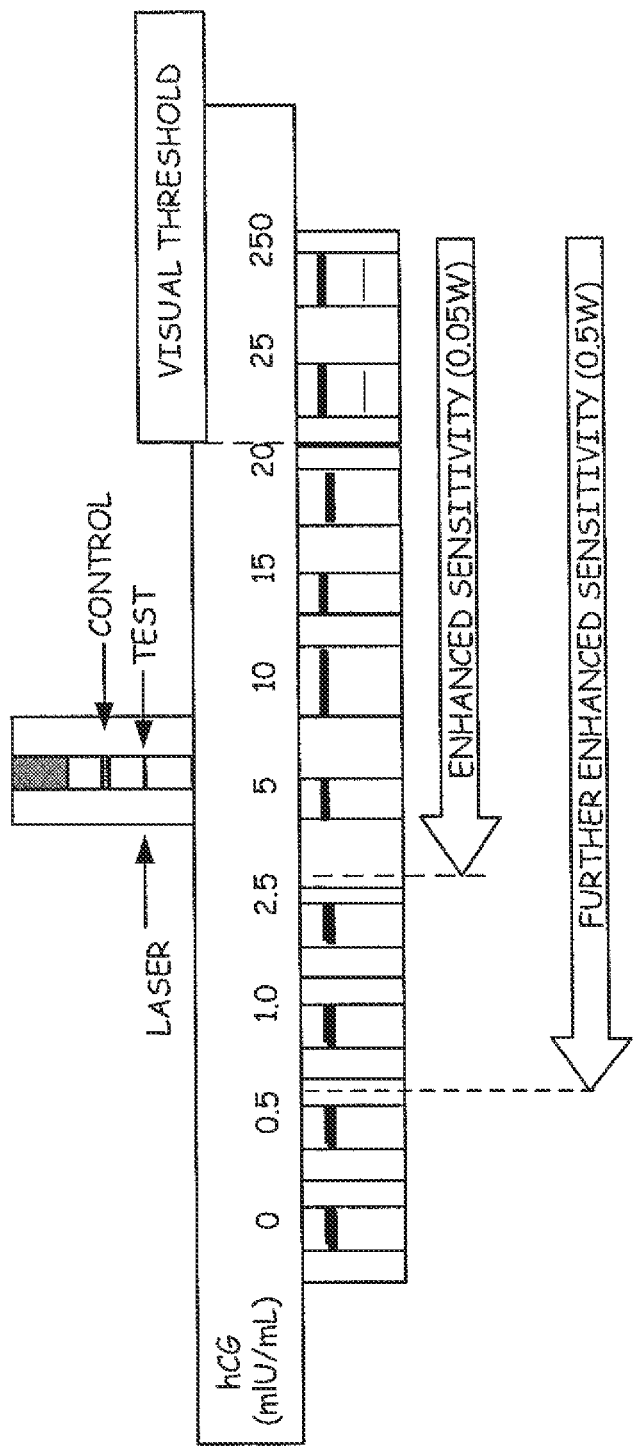
FIG. 8A is a schematic representation of a picture of results from thermal contrast assay for hCG (Human chorionic gonadotropin).
Figure 8B:
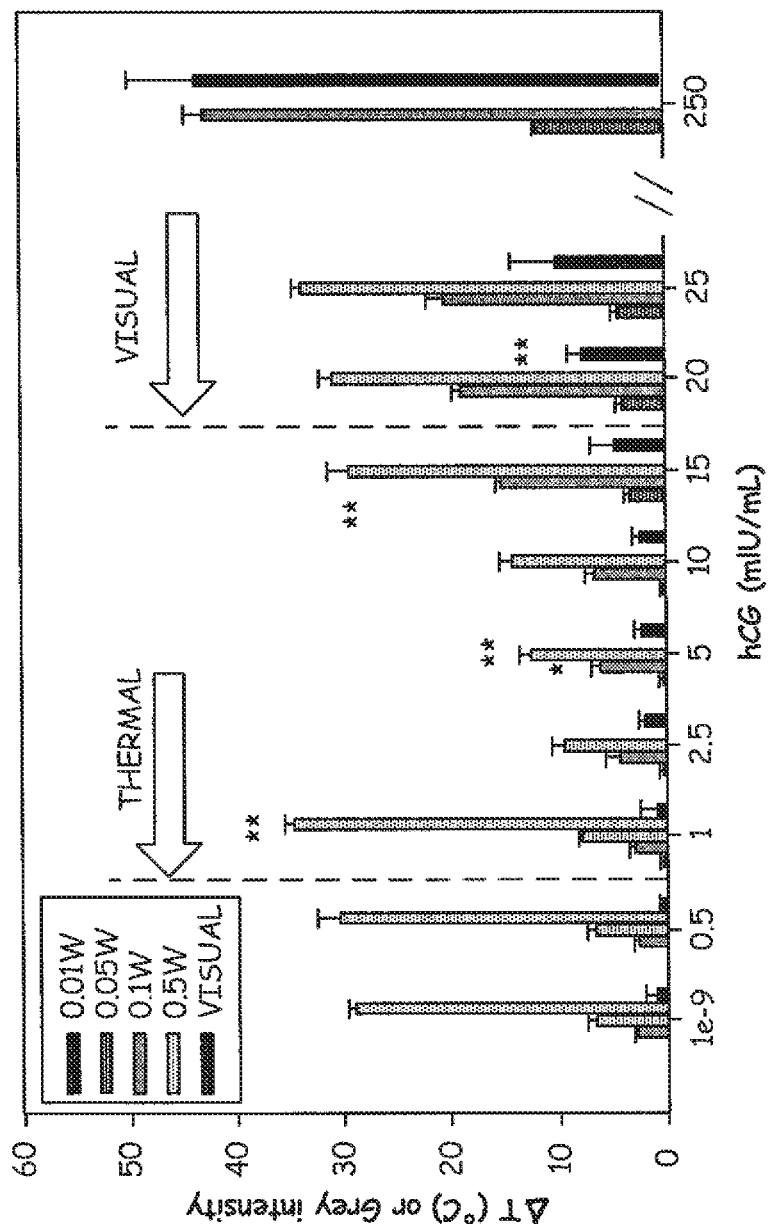
FIG. 8B is a graph of results from thermal contrast assay for hCG.

As shown in FIG. 8A and FIG. 8B, thermal contrast showed enhanced sensitivity to the presence of hCG relative to visual detection. The use of thermal contrast showed a 20-fold increase in the limit of detection.

Example 5—Detection of Malaria

The presence of the malaria antigen was also tested using a LFA with the GNPs. Malaria LFA was purchased from Alere Inc (BinaxNOW™ malaria test).

Figure 9:
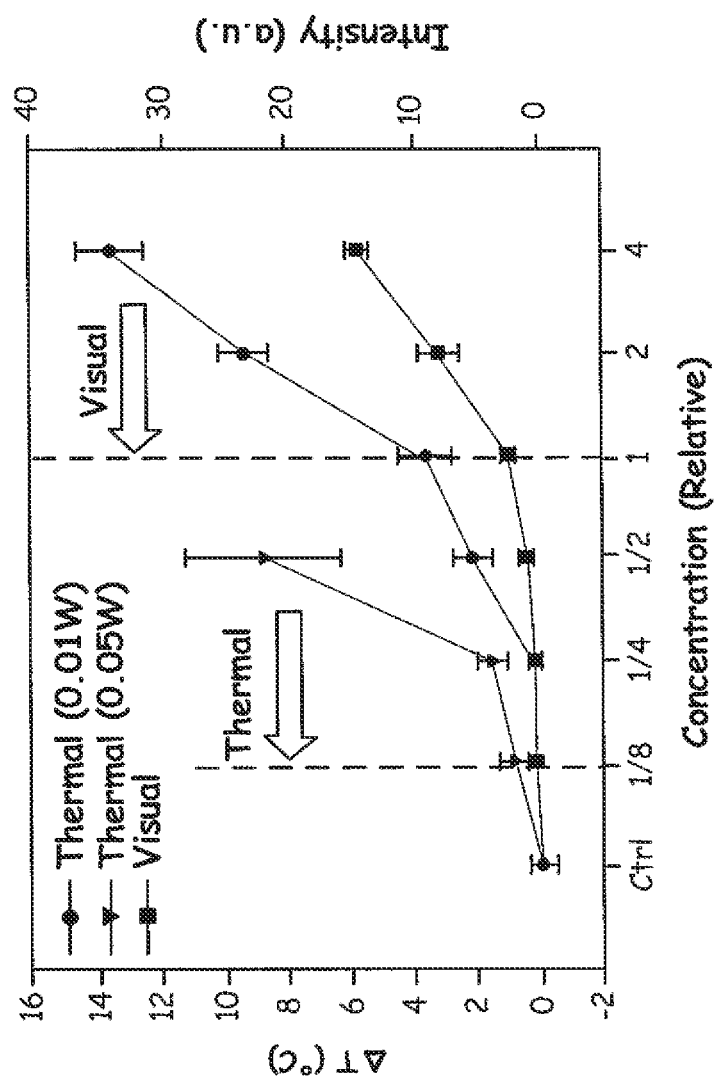
FIG. 9 is a graph of results from thermal contrast assay for malaria antigen.

As shown in FIG. 9, thermal contrast showed enhanced sensitivity to the presence of the malaria antigen relative to visual detection. The use of thermal contrast showed an 8-fold increase in the limit of detection.

Example 6—Detection of TB

The presence of TB was tested using a LFA with the GNPs. TB LFA was manufactured by Alere Inc (Determine™ TB LAM rapid test). The results are shown in Table 1. Thermal contrast detects a majority of visually negative TB LFAs (i.e. false negatives) based on reference standard of a sputum culture.

TABLE 1

| Method | Ratio Detected | Percent Detected |
|---|---|---|
| TB-LAM LFA - visual | 0/39 | 0 |
| TB-LAM LFA - thermal | 22/39 | 56 |
| Sputum Culture | 39/39 | 100 |

This directly speaks to the increase in sensitivity of the test since thermal contrast reduces the false negative test results.

Example 7—Use of Specific Absorption Rate for hCG

This experiment was conducted to see if the thermal contrast can be performed using the specific absorption rate (SAR). The thermal contrast in Examples 1-7 were performed based on $\Delta T$. The SAR is based on the initial slope of the temperature change.

Figure 10A:
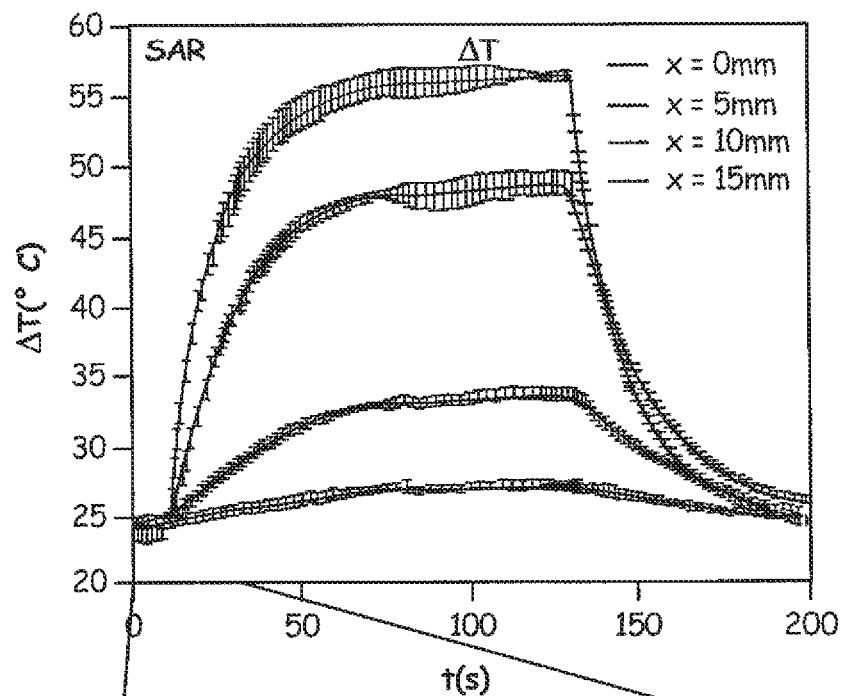
FIG. 10A and FIG. 10B are graphs illustrating the use of SAR.
Figure 10B:
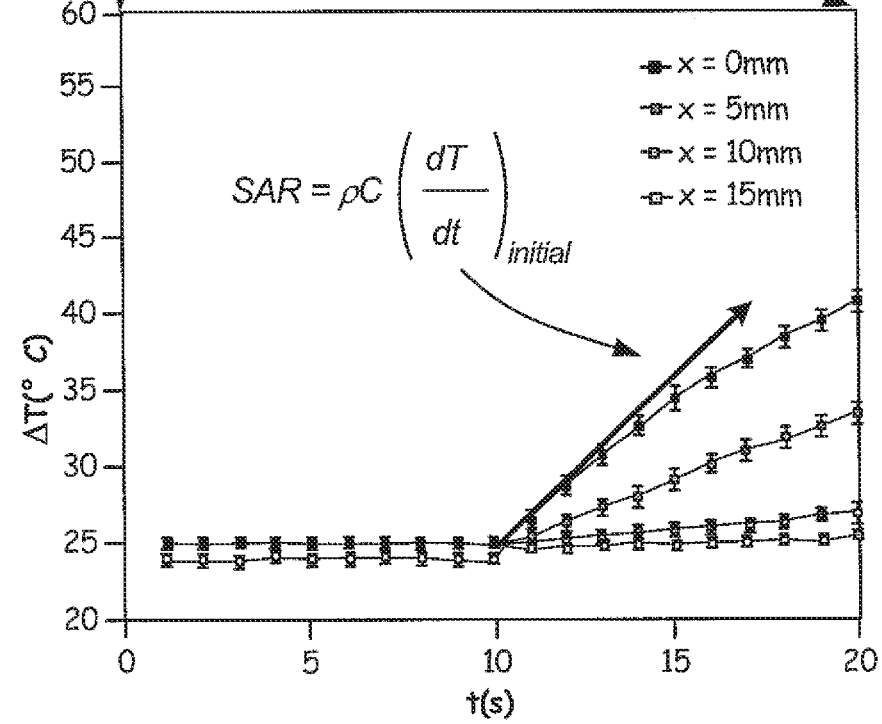
Figure 11:
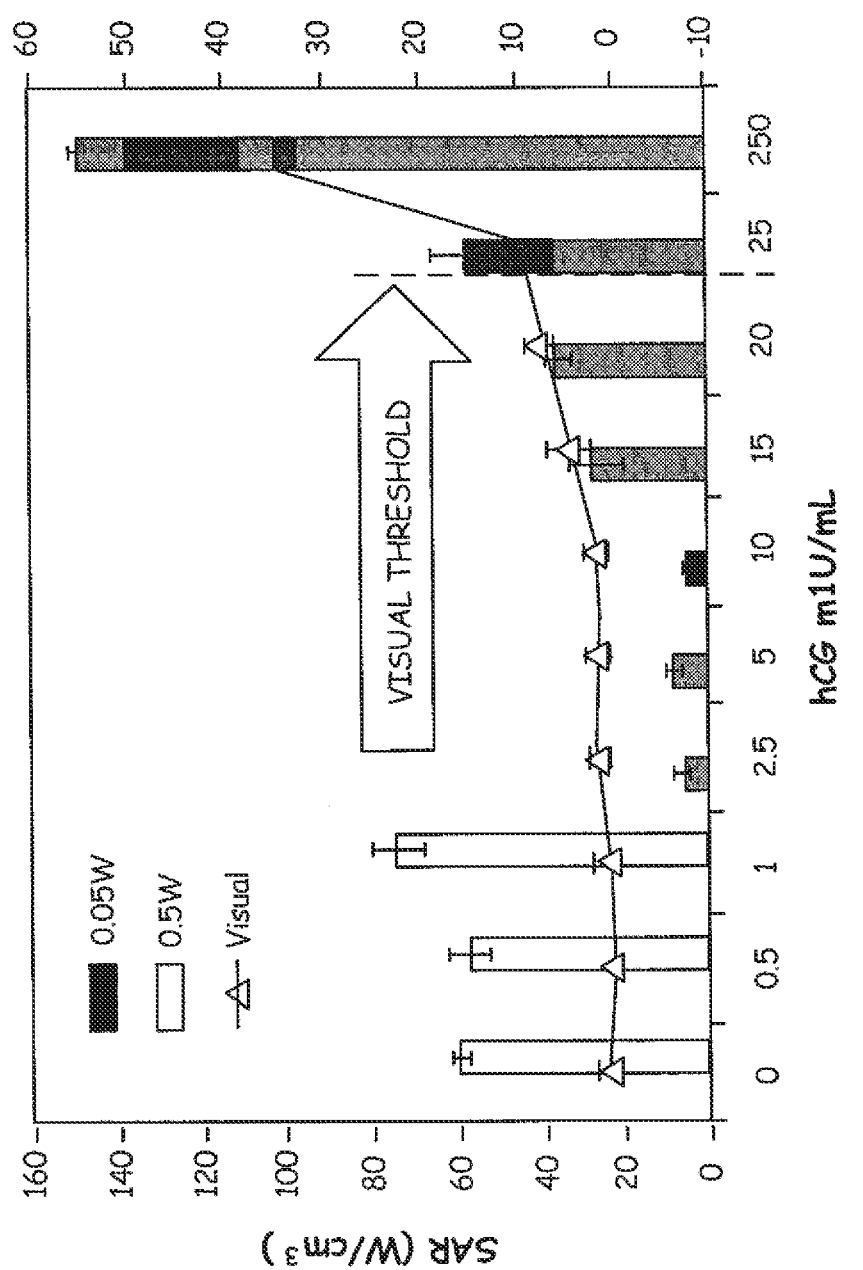
FIG. 11 is a graph of results from thermal contrast assay for hCG using SAR.

FIG. 10A shows the temperature change over an extended period of time. FIG. 10B illustrates the change in temperature in the first 20 seconds. As shown in FIG. 10A and FIG. 10B, thermal contrast can be conducted by calculating the SAR. This enables the measurement at an earlier time to minimize interference. Specifically, heat addition over time leads to diffusion in a material. If the heat can be added very quickly such that diffusion is minimized, then the rate of temperature change is related entirely to the SAR (or Q in Equation 1) and therefore can more directly capture the presence of the GNPs and thus antigen in the test. This may allow the use of a pulsed laser. FIG. 11 illustrates the results from an experiment in using hCG as described above in Example 4 except the SAR was determined instead of the temperature change. As can be seen, SAR can be used for detection of analytes without a loss of sensitivity or accuracy.

Example 8—Use of Monodisperse Particles

The nanoparticles were made as described in Example 1 using the method of Frens and analyzed for dispersity.

Figure 12C:
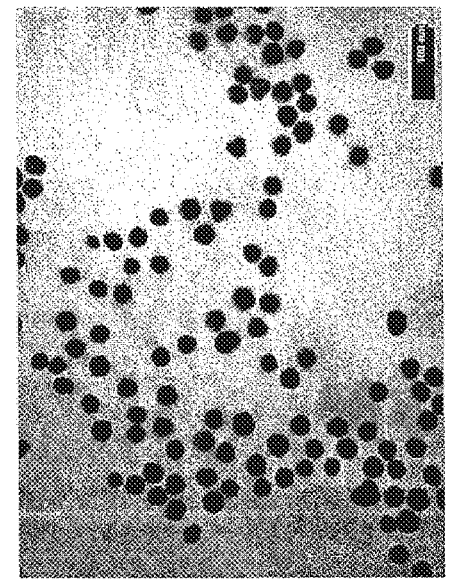
FIGS. 12A, 12B and 12C are pictures showing the polydispersity of GNPs in CrAg dipstick, hCG dipstick and synthesized GNPs, respectively.
Figure 12B:
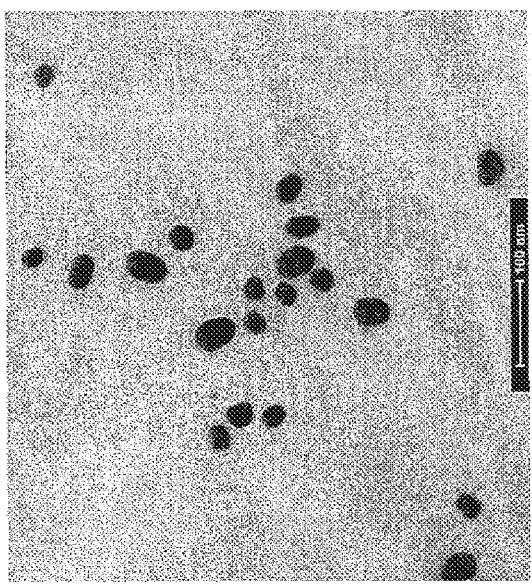
Figure 12A:
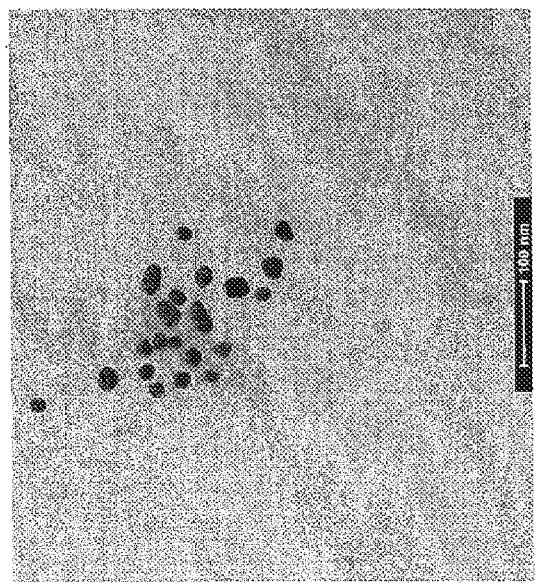

As can be seen in FIG. 12A, FIG. 12B and FIG. 12C, the synthesized GNPs are more evenly dispersed than the GNPs in the dipsticks.

Figure 13:
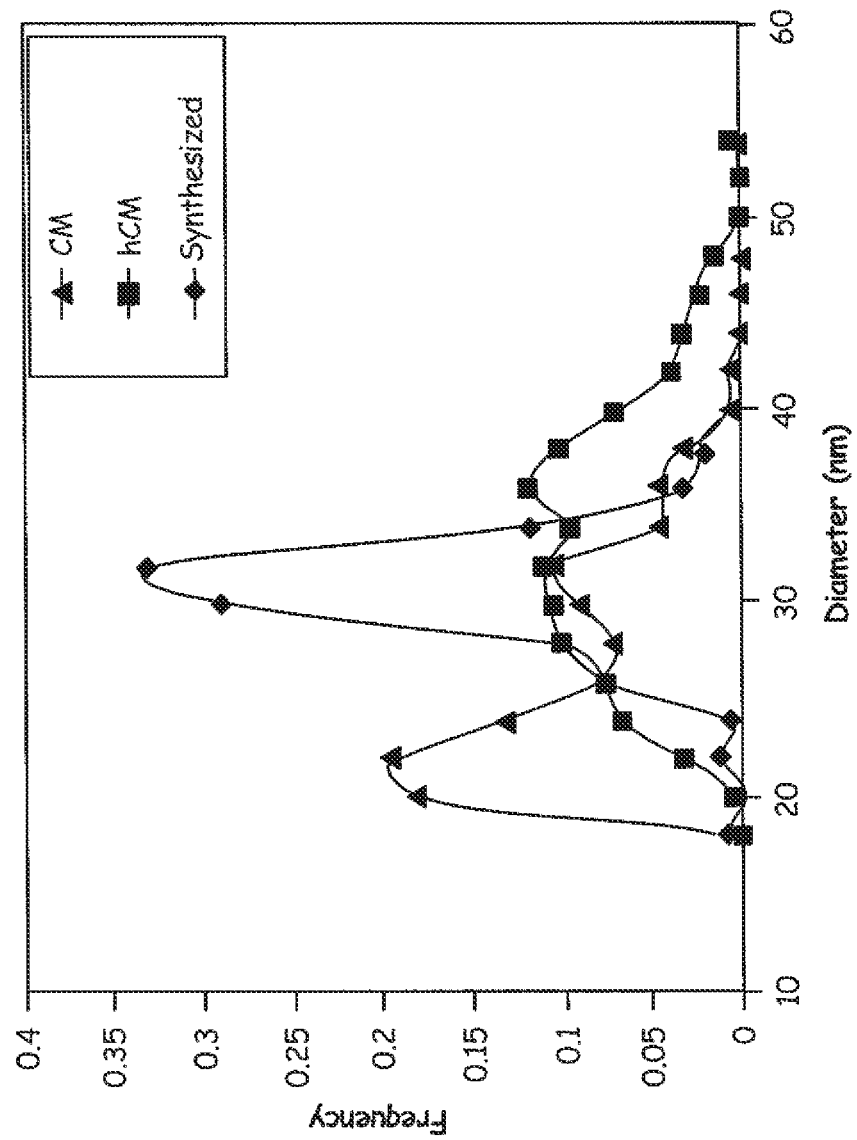
FIG. 13 is a plot of illustrating the uniform size of the synthesized GNPs.

FIG. 13 is a quantification of the results seen in the TEM images of FIG. 12. Specifically, the counts of GNPs of different sizes are added and the graph illustrates that there is a much broader distribution within the existing dipsticks vs. those synthesized by the method of Frens.

Example 9—Broad Range LFA

Synthesis and Characterization of GNPs

Monodisperse 30, 60 and 100 nm GNPs were synthesized using citrate reduction and seed mediated growth methods. (JACS 2009, 131, 17042-17043) Briefly, 15 nm seeds were synthesized as previously described by Frens et al. (Nature 1973, 241, 20-22) 100 mL of 0.25 mM $HAuCl_4$ was boiled with hot plate temperature set to 300° C. Next, 1 mL of 3% (w/v) sodium citrate was added under vigorous stirring. The 30, 60 and 100 nm GNPs were then synthesized by hydroquinone reduction of ionic gold. After synthesis, GNPs were characterized by UV-visible spectroscopy (Synergy HT, BioTek), and transmission electron microscopy (TEM, Tecnai G2).

Computation of GNP Optical Properties

Mie theory (Appl. Opt, 2001, 40, 1354-1361) was employed to compute and compare the optical properties (extinction, scattering and absorption spectrum) of GNPs in different sizes (30-400 nm). An open source Mie theory Fortran code from Oregon Medical Laser Center was utilized for GNP optical properties calculation. The surrounding media of GNP was set to water (refractive index=1.33).

Visual and Thermal Detection of GNPs in Solution

340 µl 30, 60 and 100 nm GNP solutions were loaded in a 96-well plate separately, and extinction spectra were read by UV-visible spectroscopy. The peak extinction values were utilized to determine the visual detection limit of GNPs in solution. Polystyrene cuvettes were filled with 1.5 mL of serial diluted 30, 60 and 100 nm GNP solutions separately and irradiated with 280 mW 532 mn laser (UltraLasers) from the side. The cuvettes with stirring bar inside were placed above a stirring plate to guarantee uniform temperature distribution. The temperature within cuvettes was recorded by four T-type thermocouples distributed at four corners. The solutions were heated from room temperature for 45 min to reach steady state. The temperature rise from room temperature was used to determine the thermal detection limit of GNPs in solution.

Visual and Thermal Detection of GNPs on Nitrocellulose Membrane

In order to perform a quantitative comparison of visual and thermal detection limits of different sized GNPs on LFA nitrocellulose (NC) membrane, GNPs were deposited onto the membrane uniformly, quantitatively and without aggregation. The citrate stabilized GNPs were first washed with ultrapure water (Millipore) by centrifugation twice and re-dispersed in 65% (w/w) glycerol solution. Then GNPs were printed onto NC membrane (HF135, Millipore) with a syringe pump (NE-1010, Harvard) and a 3D printer robot (Fisnar 5200N). The 3D printer robot controlled the movement of a 100 µm diameter nozzle connected to a syringe to print rectangles in spiral order. The serially diluted 30, 60 and 100 nm GNPs were printed into 2 mm×10 mm rectangles on membrane separately. The pumping rate of syringe pump was 6 µL/min and printing time for one 2 mm×10 mm rectangle was 24 s. The concentration of GNPs in membrane was determined by dividing the total number of printed GNPs with the membrane volume (2 mm×10 mm×0.13 mm). After printing, the NC membranes were dried in a vacuum desiccator placed in a 65° C. oven for one day. The dried NC membranes were then scanned (Epson XP310) and the mean greyscale intensity of rectangles was analyzed by ImageJ. The thermal contrast amplification (TCA) reader equipped with a 30 mW 532 nm DPSS laser (UltraLaser) was employed to heat printed GNPs and record their temperature changes. Pipettes and an Epson XP-310 inkjet printer were also used to print GNPs for the same purpose, however, both were inferior to 3D printing. Pipetting was used to deposit 1 μL of GNP in 65% glycerol solution onto the membrane followed by subsequent drying in a vacuum desiccator placed in a 65° C. oven for one day. The inkjet printer is unable to print with 65% glycerol solution due to high viscosity and surface tension. Thus, GNPs were dispersed in water and then printed onto membrane. Then the printed membranes were dried in ambient room environment overnight. Platinum was coated onto the membrane prior to SEM observation. The non-aggregated status of printed GNP in membrane were confirmed by SEM.

Figure 19:
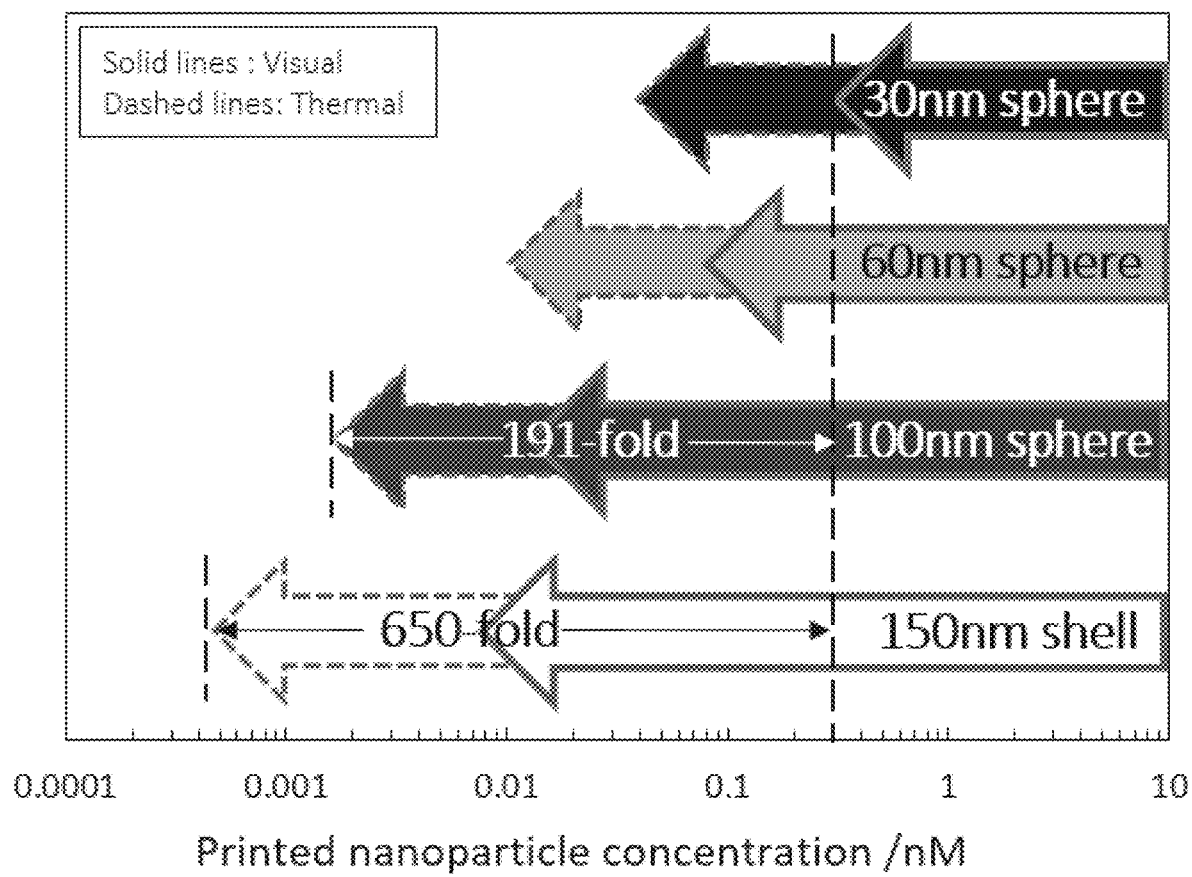
FIG. 19 is a graph of experimental results of thermal and visual detection limits of 150 nm nanoshells, 30 nm, 60 nm, 100 nm nanospheres.

NC membranes were also printed with 150 nm gold nanoshells. The visual and thermal responses were compared to the 30 nm, 60 nm, and 100 nm spheres as shown in FIG. 19. The 150 nm gold nanoshells showed a 650-fold sensitivity improvement using thermal contrast over 30 nm gold nanoparticles using usual contrast as seen in FIG. 19.

Measurement of LFA Flow Velocity

Half strips consisting of only porous membranes and absorbent pads with backing material were employed in the flow velocity measurement studies. The dimensions of half strip membrane and absorbent pad were both 3 mm×20 mm, which are the same as in streptavidin/biotin LFAs and CRP LFAs. The flow in the LFAs were divided into two consecutive phases: "membrane" and "absorbent pad" phase. For "membrane" phase velocity measurement, half strip was dipped into a red dye reservoir and the flow was recorded by a camera. The position of red liquid front was extracted from the recorded video based on the greyscale intensity difference in the vicinity of liquid front by a customized Matlab script. The "absorbent pad" phase velocity was obtained by tracing the front of dye pulses generated by alternately dipping pre-wetted half strips in a red dye reservoir for 2 s, and a water reservoir for 200 s. Thus, three pulses were generated for each half strip and recorded with a digital camera. The "membrane" phase flow is initially higher and then falls while the "absorbent pad" phase is more constant. Similarly, the position of a dye pulse front was identified by a customized Matlab script. The "membrane" phase velocity measurement was compared with the Washburn equation. Three types of membranes with different pore sizes including HF75, HF135 and HF240 (Millipore) were tested. Also, the effect of membrane length on flow velocity was studied between 2 and 4 cm where 2 cm is a standard length, and 4 cm would be unusually long. Further, as membrane length increases, the "absorbent pad" phase velocity decreases due to the increased viscous resistance associated with longer membrane length.

Functionalization of GNP Surface

Streptavidin and biotin binding was selected owing to the strong interaction with extremely low dissociation constant $K_d=10^{-14}$ M.[5] As small molecules such as biotin can't bind to nitrocellulose membrane directly, BSA-biotin complex was used. 10 μL of 10 mg/mL streptavidin (Sigma) was added to 1 mL of 30, 60 and 100 nm GNP solution, respectively. The mixture was incubated for 60 min, then 10 μL of 10 mg/mL BSA (Sigma) was added and the mixture was further incubated for 20 min. The GNPs were washed through centrifugation twice to remove unbound protein. The solution was stored at 4° C. prior to use.

Fabrication and Test of Streptavidin/Biotin LFAs

The LFAs were composed of conjugate pad (GE Healthcare), NC membrane (HF135, Millipore) and absorbent pad (GE Healthcare). The conjugate pad is treated with 0.01 M PBS (pH=7.4), 1% (w/v) sucrose, 0.5% (w/v) BSA, 0.01% (v/v) Tween 20 and dried at 37° C. in a humidity chamber (RH=20%) for 2 hrs. The conjugate pad, membrane and absorbent pad were then assembled onto a polyester adhesive backing, allowing 1-2 mm overlap between adjacent components to facilitate the migration of solution. The assembly was laminated and cut into individual strips with 3 mm width.

Test dots were prepared by pipetting 0.5 μL of 4 mg/mL BSA-biotin (Sigma) onto the NC membrane. Functionalized 30, 60 and 100 nm GNPs were 2-fold serially diluted and 10 μL of each was added to the conjugate pad per LFA. The LFAs were dried at 37° C. in a humidity chamber (RH=20%) for 2 hrs and stored at 25° C. in a humidity chamber (RH=20%) prior to use. The tests were performed by dipping LFAs into 96-well plates filled with 150 μL 0.01 M PBS (pH=7.4). The visual signals of the LFAs were obtained by averaging test dot greyscale intensities of scanned LFA images using ImageJ. A TCA reader with 30 mw 532 nm laser was used to record the thermal signal along the longitudinal center line of NC membrane.

Figure 20:
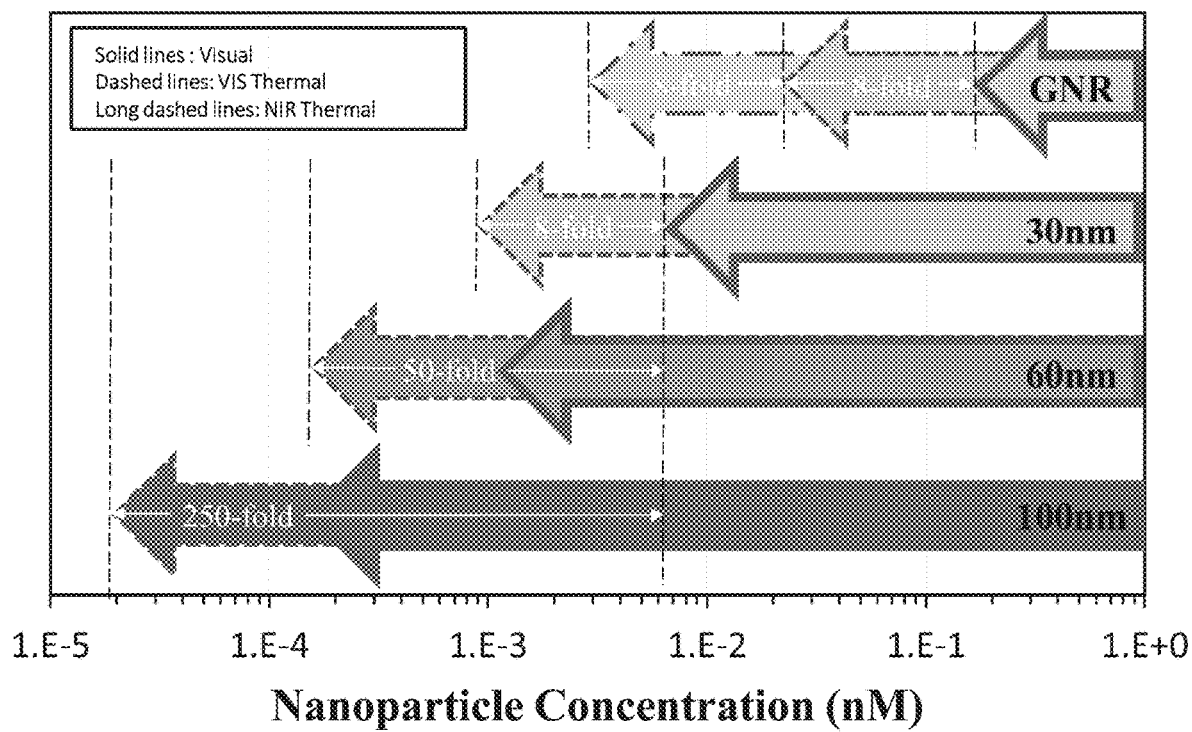
FIG. 20 is a graph of experimental thermal and visual detection limits of streptavidin/biotin LFAs with gold nanorods, 30, 60 and 100 nm GNPs. The gold nanorods were excited with 532 nm or 780 nm laser excitation.

Gold nanorods were tested with streptavidin-biotin. Gold nanorods were 8*30 nm and were printed onto nitrocellulose membrane. The thermal signal was measured with both 532 nm and 780 nm 30 mW laser. The results are shown in FIG. 20. The results show a 2-fold sensitivity improvement using gold nanorod with a 780 nm laser excitation compared to 30 nm gold nanosphere with visual detection.

C-Reactive Protein LFAs

Two, 2, and 1 μL of anti-CRP (Medix Biochemica) was added to 1 mL of 30, 60 and 100 nm GNP solution, respectively. The mixture was incubated for 60 min at 4° C. Then 10 μL of 10 mg/mL BSA (Sigma) was added and incubated for 20 min. The GNPs were washed through centrifugation twice to remove unbound proteins. The conjugate pad was treated with 0.01 M PBS (pH=7.4), 1% (w/v) sucrose, 0.5% (w/v) BSA, 0.01% (v/v) Tween 20 and dried at 37° C. in a humidity chamber (RH=20%) for 2 hrs. The conjugate pad, membrane and absorbent pad were then assembled onto a polyester adhesive backing, allowing 1~2 mm overlap between adjacent components. The assembly was cut into 3 mm width individual strips. Then 0.4 μL of 0.27 mg/mL anti-CRP (Medix Biochemica) was pipetted onto membrane as test dot, and 0.4 μL of 1 mg/mL anti-mouse IgG (Abcam) was added onto membrane as a control dot. 10 μL functionalized 30, 60 and 100 nm GNPs in the same concentration were used per LFA (i.e., 6×10$^8$ GNPs per LFA). The LFAs were dried and stored in a controlled humidity chamber (RH=20%) prior to use. Standard human CRP reference (HyTest) was 2-fold serially diluted with 10 mM PBS. LFAs were dipped into 96-well plates filled with 150 μL CRP samples. Visual and thermal signals of CRP LFAs were obtained using the same methods as for streptavidin/biotin LFAs. Also, one clinical serum sample, with CRP concentration 186 mg/L, was 2-fold serially diluted with 10 mM PBS and then tested with fabricated LFAs.

Scaling and Modeling of GNPs

Scaling and modeling was performed to investigate the impact of nanoparticle size in LFA analytical performance. The modeling helped to identify key parameters such as GNP size and concentration, reaction rate constant and flow speed that determine the analytical performance of LFAs. FIG. 14A is a diagram wherein Pe is the ratio of diffusion time to convection time of a GNP, Pe>>1 in LFA implies the transport is diffusion-limited, Da is the ratio of reaction flux to diffusion flux, Da<<1 in LFA implies the rate limit is reaction. FIG. 14B is a diagram comparing 30 nm, 60 nm and 100 nm GNPs and indicates 100 nm GNPs can improve LFA sensitivity due to higher reaction rate and signal per GNP.

Figure 15B:
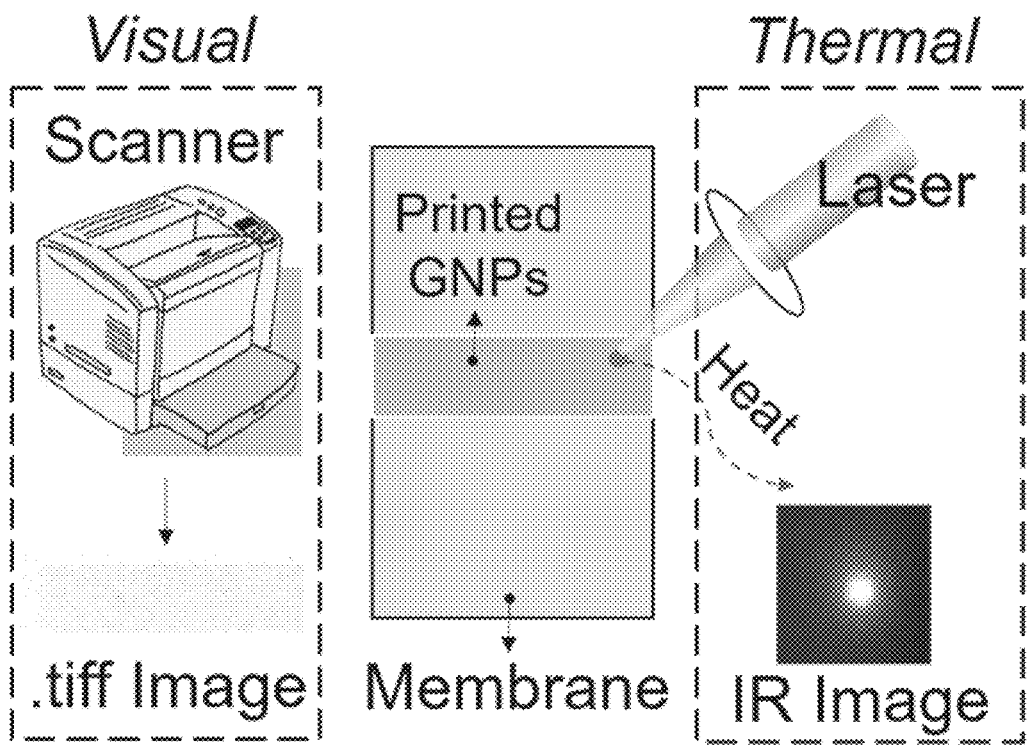
FIG. 15B is diagram of the visual and thermal detection of printed GNPs.
Figure 15C:
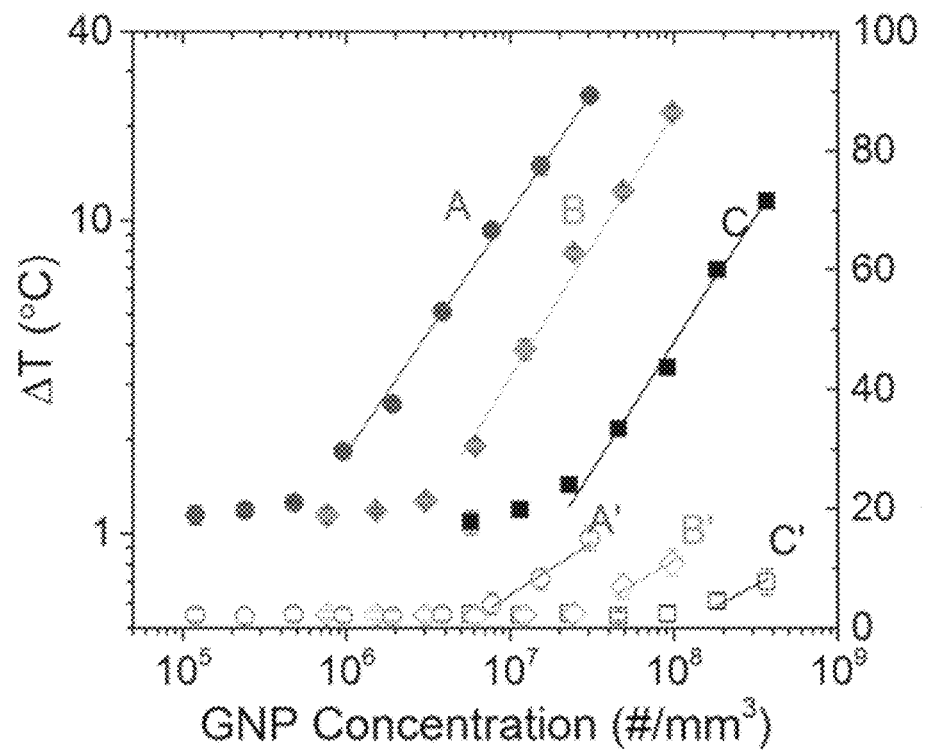
FIG. 15C is a graph of quantitative thermal and visual detection of 30, 60 and 100 nm GNPs, where A, A' stand for 100 nm thermal and visual signal, B, B' for 60 nm thermal and visual signal, C, C' for 30 nm thermal and visual signal, respectively.
Figure 15D:
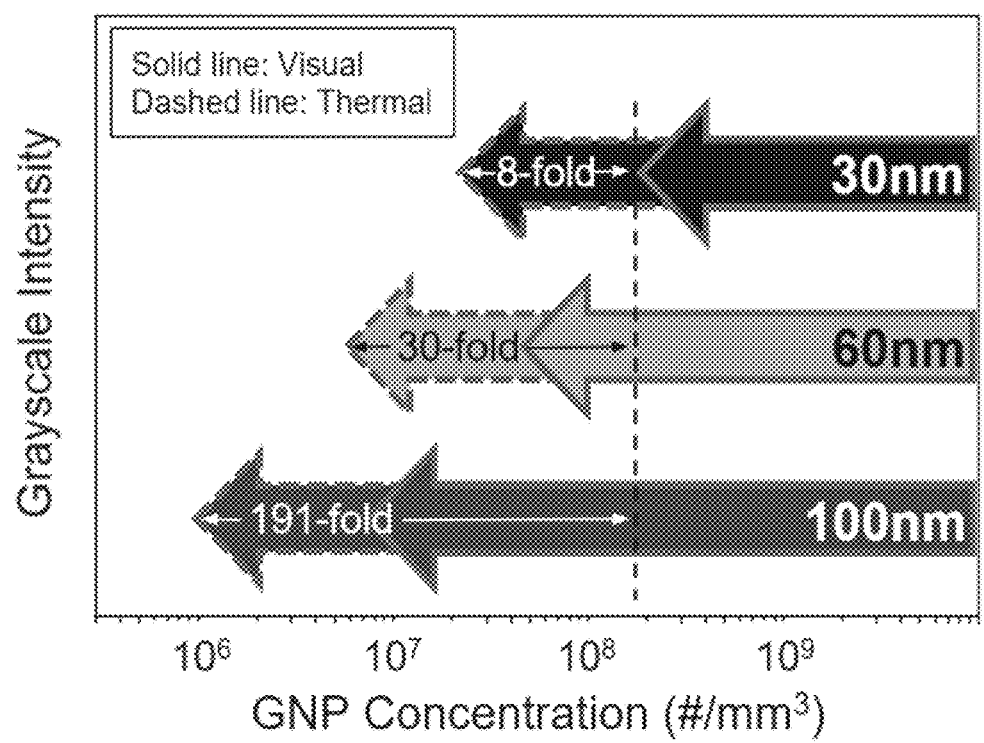
FIG. 15D is a graph of thermal and visual detection limits of printed 30, 60 and 100 nm GNPs.

FIG. 15B is diagram of the visual and thermal detection of printed GNPs. FIG. 15C is a graph of quantitative thermal and visual detection of 30, 60 and 100 nm GNPs, where A, A' stand for 100 nm thermal and visual signal, B, B' for 60 nm thermal and visual signal, C, C' for 30 nm thermal and visual signal, respectively. FIG. 15D is a graph of thermal and visual detection limits of printed 30, 60 and 100 nm GNPs.

Two LFA cases were studied: Case 1. diffusion, convection and direct GNP binding LFA (biotin-streptavidin), and Case 2. diffusion, convection and sandwich GNP binding LFA with C-reactive protein (CRP) as analyte.

The Peclet number (Pe) and the Damkohler number (Da) were scaled for these cases to assess the importance of diffusion to convection and reaction in the LFAs (FIG. 14A). The effective forward reaction constant ($k_{on}'$) for antibody labelled GNPs is assumed to be:

$$k_{on}' = n \cdot k_{on} \quad \text{Equation (2)}$$

where $k_{on}$ is the forward rate constant for a single antibody-antigen interaction in the LFA membrane environment, and n is the effective number of antibodies that bind the test line per GNP. With the calculated Pe>>1 (convection dominates diffusion) and Da<<1 (diffusion dominates reaction) shown in Table 2, thus reaction is the rate limiting step to improve GNP capture. The larger size GNPs (60 and 100 nm) show both improved label contrast (visual or thermal, FIG. 15C), and improved GNP capture as n increases in Eqn.2 due to larger surface area.

TABLE 2

| | 30 nm | 60 nm | 100 nm |
|---|---|---|---|
| Effective Diffusivity ($D_e = \Box D)/m^2s^{-1}$ | $1.2 \times 10^{-11}$ | $5.8 \times 10^{-12}$ | $3.5 \times 10^{-12}$ |
| Estimated maximum number of antibodies per GNP (m) | 17 | 68 | 189 |
| Effective forward constant ($k_{on}' = nk_{on}$)/$M^{-1}s^{-1}$ | $1.24 \times 10^4$ | $4.95 \times 10^4$ | $1.37 \times 10^5$ |
| Pe = UR/$D_e$ | 85 | 171 | 284 |
| Da = $k_{on}$CR/$D_e$ | $5.28 \times 10^{-3}$ | $4.22 \times 10^{-2}$ | $1.95 \times 10^{-1}$ |

A COMSOL model was developed to extend the above scaling analysis and predict LFA performance prior to experiments thus guiding LFA design for both Cases. Consistent with the scaling analysis, the model shows that reaction is the key to improving GNP capture. COMSOL software was purchased from COMSOL, Inc. Burlington, Mass. and used to model the diffusion, convection and reaction processes in LFA.

Figure 16A:
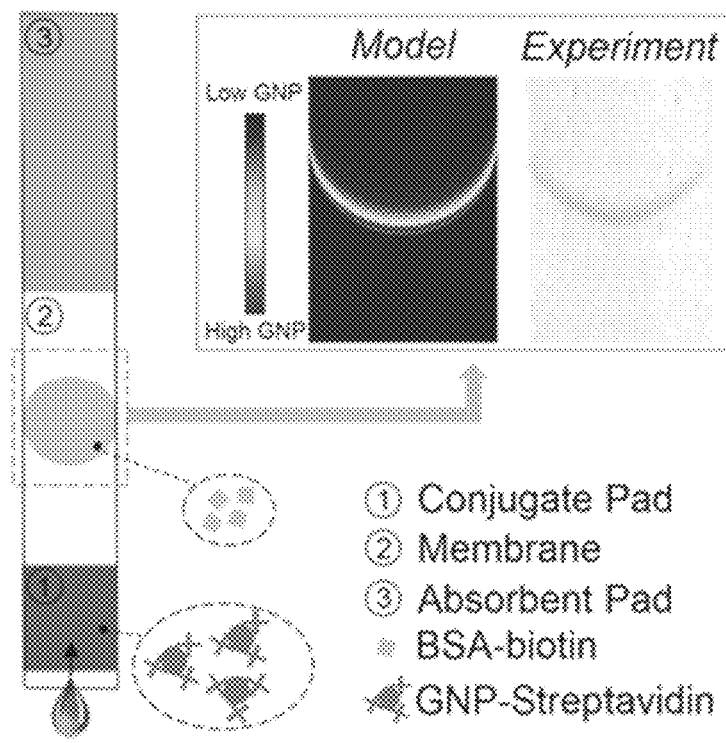
FIG. 16A is a schematic diagram of streptavidin/biotin LFAs. The insert are the experimental and modeling results of the LFA test.
Figure 16B:
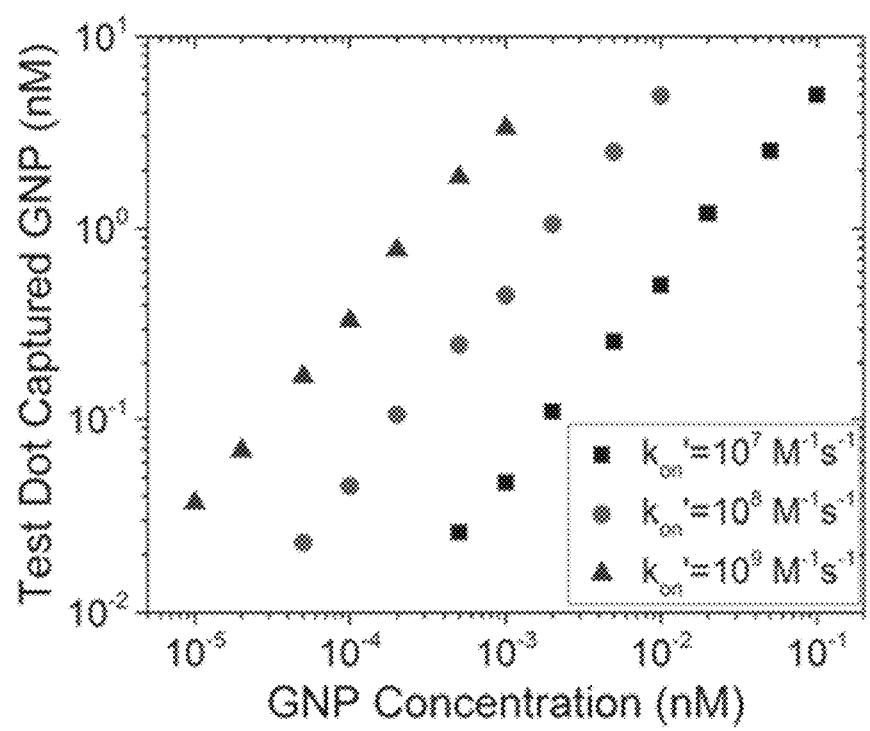
FIG. 16B is plot of modeling results of quantitative 30 nm GNP capture for different effective forward reaction constant values.
Figure 16C:
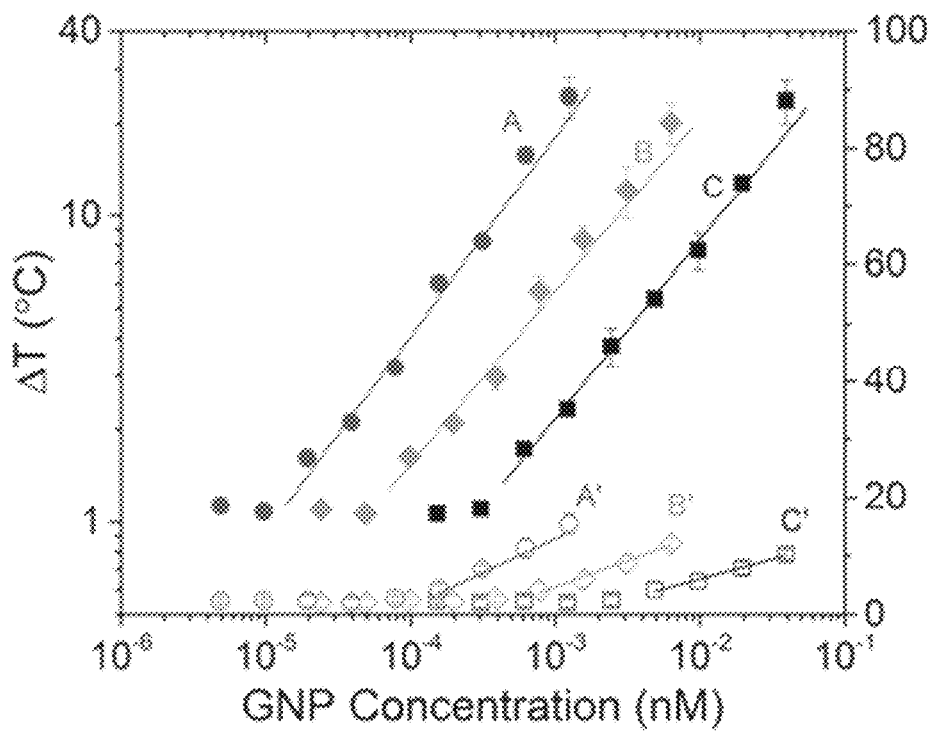
FIG. 16C is a plot of experimental thermal and visual signals of 30, 60 and 100 nm GNP streptavidin/biotin LFAs, A, A', B, B', C, C' share the same legends as in FIG. 15C.
Figure 16D:
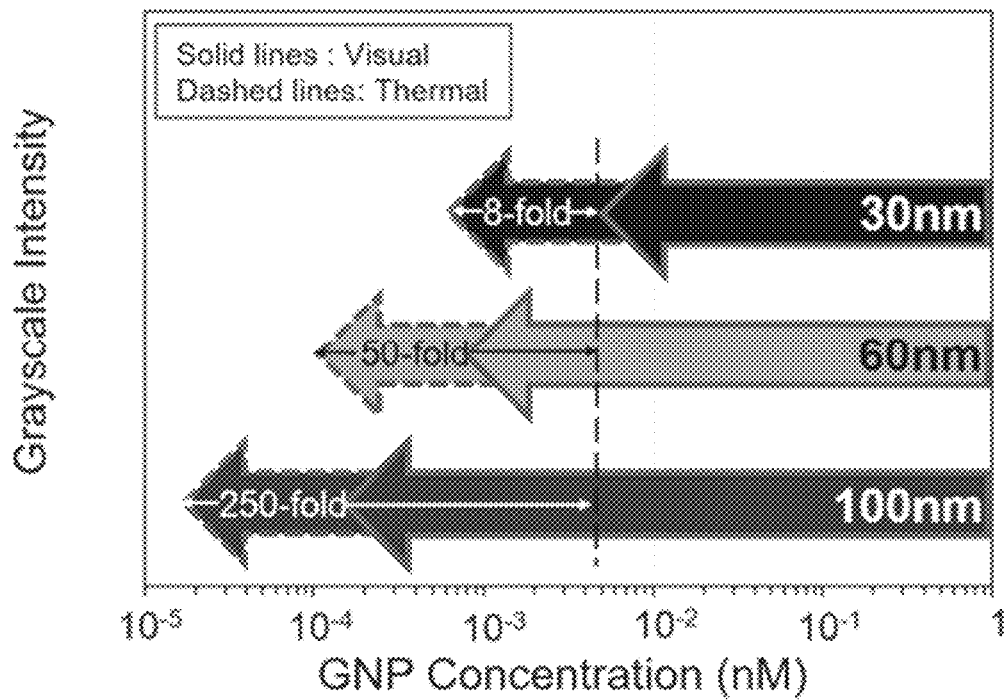
FIG. 16D is a graph of experimental thermal and visual detection limits of streptavidin/biotin LFAs with 30, 60 and 100 nm GNPs.

In Case 1, COMSOL was used to model direct binding of streptavidin coated GNPs to the biotin coated test dot (FIG. 16A). FIG. 16A is a schematic diagram of streptavidin/biotin LFAs. The inserts are the experimental and modeling results of the LFA test. FIG. 16B is plot of modeling results of quantitative 30 nm GNP capture for different effective forward reaction constant values. FIG. 16C is a plot of experimental thermal and visual signals of 30, 60 and 100 nm GNP streptavidin/biotin LFAs, A, A', B, B', C, C' share the same legends as in FIG. 15C. FIG. 16D is a graph of experimental thermal and visual detection limits of streptavidin/biotin LFAs with 30, 60 and 100 nm GNPs. The results show that larger size GNPs can be detected at lower concentrations in streptavidin/biotin LFAs. The model predicted that the majority of the GNP are captured at the front arc of the test dot due to high binding affinity ($K_d=10^{-14}$M) of the excess biotin to the streptavidin (FIG. 16A). In FIG. 16B, the model predicted the GNP capture increases as $k_{on}'$ increases, indicating sensitivity improvement with larger GNP (larger $k_{on}'$).

To experimentally test Case 1 model predictions, streptavidin was conjugated to GNPs to bind a test dot coated with excess biotin in the LFA. As predicted by the model, only a red arc at the test dot edge was observed after an LFA test. The quantitative correlation between GNP concentration and thermal signal ($R^2>0.96$), as well as visual signal ($R^2>0.95$) are presented in FIG. 16C. A 250-fold improvement in sensitivity is illustrated in FIG. 16D for thermal detection of 100 nm GNP over visual detection of 30 nm GNP. $k_{on}'$ of different size GNPs was fitted using the thermal signal ($\Delta T$) of test dots and the "$\Delta T$ to GNP concentration" calibration curves (FIG. 15C). The results indicate that 100 nm GNPs have more than 3-fold higher $k_{on}'$ than 30 nm GNPs ($2.5 \times 10^7$ vs. $7.5 \times 10^6 M^{-1}s^{-1}$), implying that larger GNPs have higher n in Eqn.(2).

Figure 17B:
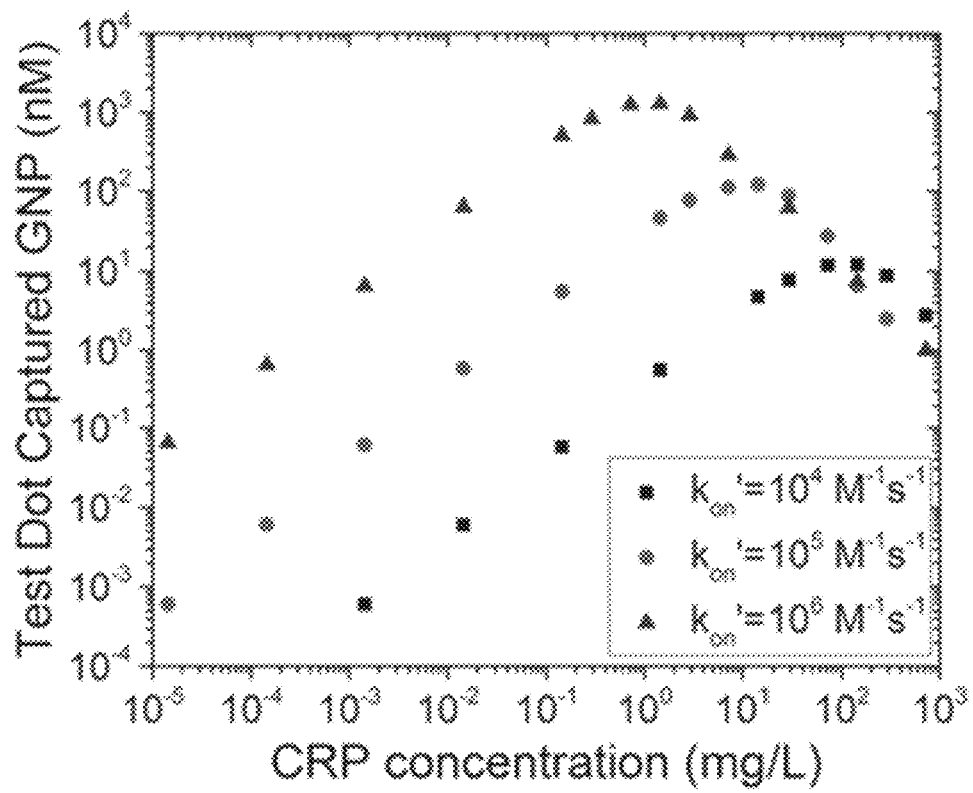
FIG. 17B is a plot of modeling results of quantitative 30 nm GNP capture for different effective forward reaction constant values.
Figure 17C:
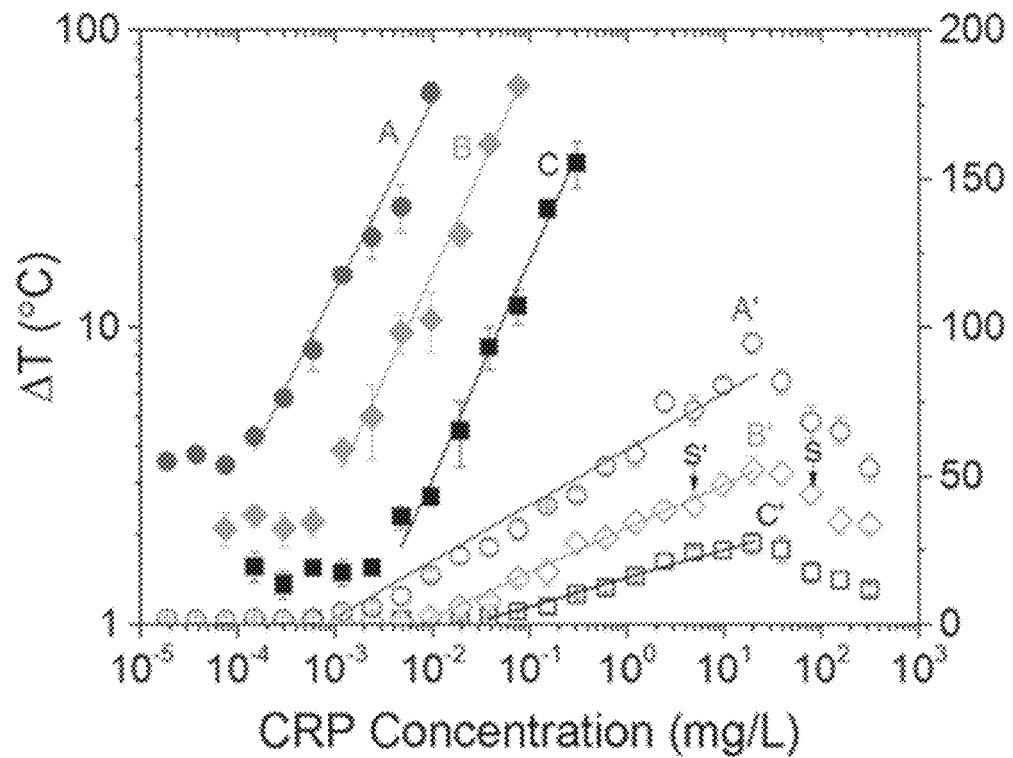
FIG. 17C is a plot of experimental visual and thermal signals of CRP LFAs, A, A', B, B', C, C' share the same legends as in FIG. 15C.

In Case 2, COMSOL was used to model sandwich binding of GNP in the test dot of a CRP LFA. Different test dot patterns were noted for different CRP concentration, indicating semi-quantitative visual readings (FIG. 17A). These test dot patterns show that they can be used to expand the LFA analytical range beyond the "hook" effect which occurs at excessively high analyte concentrations, leading to a reduction in GNP capture. For instance, the model predicted different test dot patterns (before and after the "hook" effect) such that S can be distinguished from S' albeit they have the same visual signal averaged across the dot (FIG. 17A and FIG. 17C). Importantly, the model also revealed that this approach requires $k_{on}'>10^3 M^{-1} s^{-1}$ which suggests a failure criterion when using low affinity antibodies or sparsely coated GNP labels. The sensitivity and linear quantitation range (before the "hook" effect) of the LFA also depends on $k_{on}'$ (FIG. 17B). For instance, using the thermal detection limit of 100 nm GNPs ($1.6 \times 10^{-3}$ nM), a >5 $\log_{10}$ linear visual detection range could be expected when $k_{on}'=10^4$ $M^{-1}s^{-1}$, while a >6 $\log_{10}$ linear detection range could be expected when $k_{on}'=10^5$ $M^{-1}s^{-1}$ (FIG. 17B).

Figure 17D:
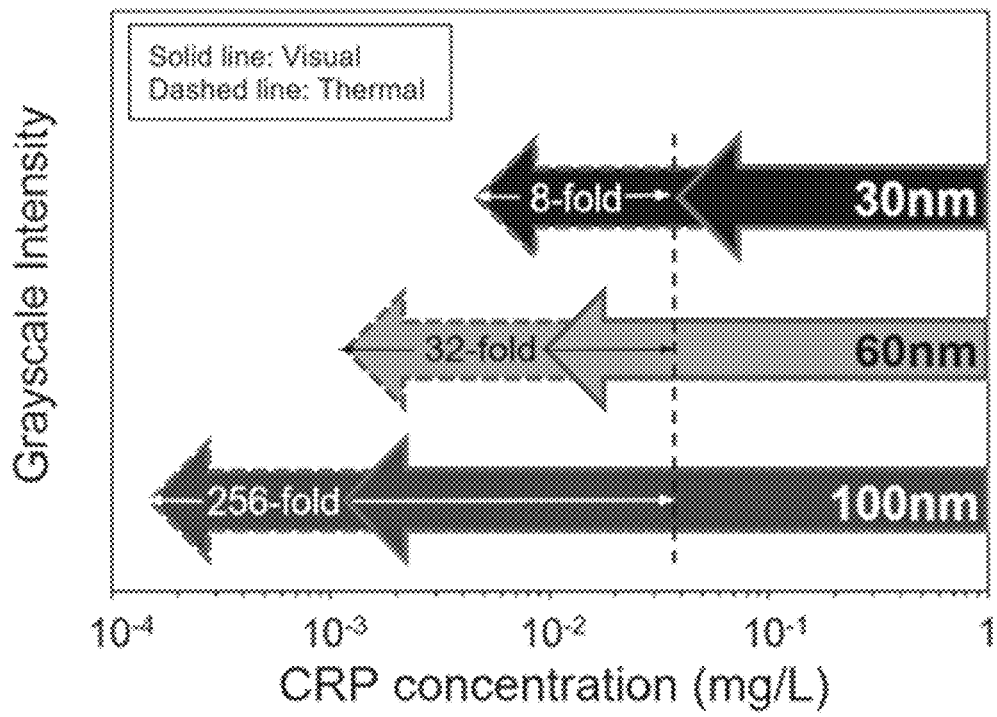
FIG. 17D is a graph of experimental thermal and visual detection limits of CRP LFAs with 30, 60 and 100 nm GNPs.
Figure 18:
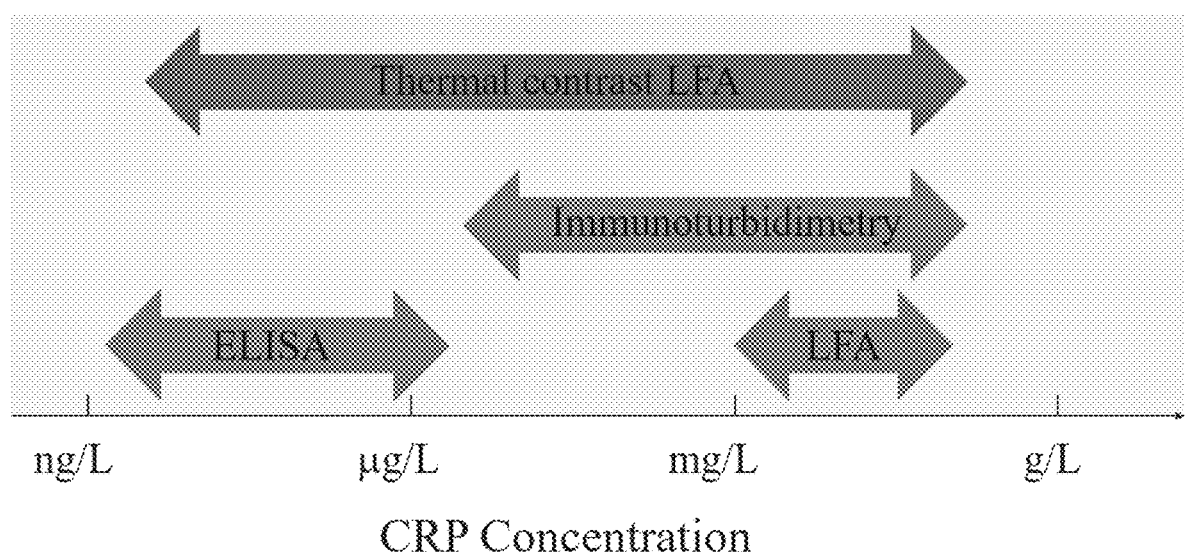
FIG. 18 is a illustrating the wide detection range of thermal contrast LFA compared to other types of assays.

A sandwich LFA was constructed to detect CRP, an important clinical biomarker of inflammation. Then dilution testing was performed with standard human CRP reference (HyTest, Finland). FIG. 17A is a schematic of modeling and experimental results of test dot visual reading and "hook" effect compensation. FIG. 17B is a plot of modeling results of quantitative 30 nm GNP capture for different effective forward reaction constant values. FIG. 17C is a plot of experimental visual and thermal signals of CRP LFAs, A, A', B, B', C, C' share the same legends as in FIG. 15C. FIG. 17D is graph of experimental thermal and visual detection limits of CRP LFAs with 30, 60 and 100 nm GNPs. The results show that the combination of 100 nm GNPs and TCA reader provides 256 fold sensitivity improvement in CRP LFAs. The different patterns of test dot binding (bottom to top in flow) as predicted by the model enable the detection before and after the "hook" effect. This effectively extends the visual analytical range to 5 $\log_{10}$ ($10^{-3}$ mg/L to >$10^2$ mg/L) using 100 nm GNPs (FIG. 17C). Further, thermal contrast achieves one $\log_{10}$ sensitivity improvement over visual contrast for all GNP sizes, including 30 nm as previously shown in commercial LFAs. In sum, the 100 nm GNP yields a 256-fold sensitivity improvement using thermal detection, versus traditional 30 nm GNP visual detection (FIG. 17D).

To improve translation and demonstrate clinical use, a human patient serum sample was also tested. The results aligned well with the calibration curves obtained with standard human CRP reference samples. Similar to Case 1,100 nm GNPs were found to have a more than 2-fold higher $k_{on}'$ than 30 nm GNPs ($6.5 \times 10^4$ vs. $2.8 \times 10^4 M^{-1} s^{-1}$). Further, the ratio of $k_{on}'$ (100 nm vs. 30 nm GNP) in Case 1 is greater than the ratio in Case 2. This can be attributed to the extra curvature and molecular length that would impede binding in sandwich (Case 2) vs. direct binding (Case 1).

Increasing gold nanosphere size above 100 nm could further increase LFA sensitivity. However, GNP capture can be rate limited by diffusion (Da>>1) as $k_{on}'$ increases with GNP size, therefore further increasing GNP size can decrease GNP capture as larger GNPs have slower diffusion rate. In addition, the increased cost and chances of non-specific binding (i.e. false-positive) of larger GNPs suggest that there may exist a size above which the sensitivity no longer increases.

GNP design was examined, specifically how size and contrast (visual vs. thermal) affects LFA analytical performance. The transport and reaction processes in the LFA were scaled and modeled. It was found that the sensitivity greatly depends on the GNP binding process. The model can predict LFA performance based on nanoparticle design, thus helping to reduce excessive experimentation and more quickly identify and experimentally verify optimum LFA designs. For instance, the model shows that larger size GNPs have higher binding affinity and can be detected at lower concentration. Using 100 nm GNPs with thermal contrast detection, the LFAs were then experimentally verified to detect CRP over roughly 6 $\log_{10}$ concentration range, spanning the range of both laboratory and POC CRP assays on the market in one simple test.

Thus, modified GNP labels with both visual and thermal contrast detection can be used to create a point of care (POC) diagnostic platform that is competitive in sensitivity, analytical range and quantitation with laboratory based technologies.

Example 10-Broad Range LFA with Larger Size GNPs

GNP particles were prepared and characterized as described above in Example 9.

Figure 21A:
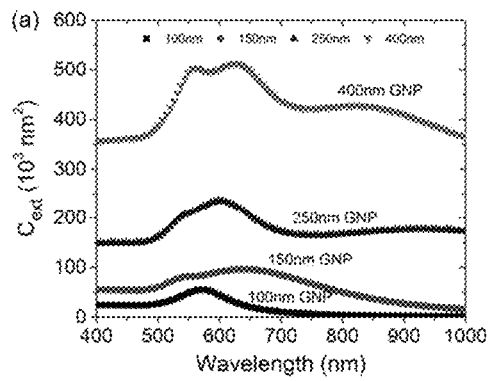
FIGS. 21A-C are graphs of theoretical predictions of optical properties of large size GNP (100-400 nm).
Figure 21B:
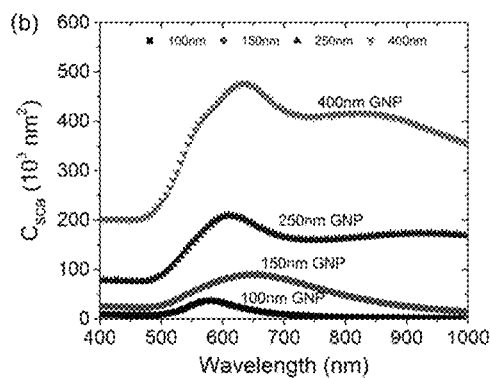
Figure 21C:
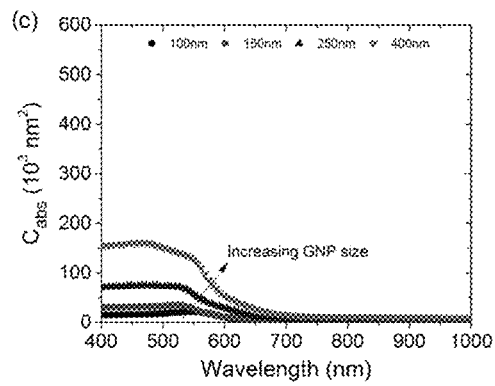

The feasibility of using larger size GNP (above 100 nm) was examined and their impact on LFA analytical performance. As the largest size of commercially available monodispersed GNP is 400 nm (Sigma), the size range of 100-400 nm was selected. Mie theory was used to calculate the optical properties of different GNP sizes (100, 150, 250 and 400 nm). FIG. 21A shows that the extinction cross section area ($C_{ext}=C_{sca}+C_{abs}$) increases as GNP size increases. FIG. 21B shows that the scattering cross section area ($C_{sca}$) increases as GNP size increases, indicating stronger visual contrast signal for larger size GNPs. FIG. 21C shows that the absorption cross section area ($C_{abs}$) at 532 nm (green laser) increases as GNP size increases, indicating stronger thermal contrast signal for larger size GNPs. In addition, the absorption cross section area ($C_{abs}$) rises with growing GNP size, specifically, a 7-fold increase of $C_{abs}$ at 532 nm for 400 nm GNP over 100 nm GNP. These enhanced visual and thermal signals of larger GNPs suggest that increasing GNP size above 100 nm will further improve GNP detection.

Figure 24A:
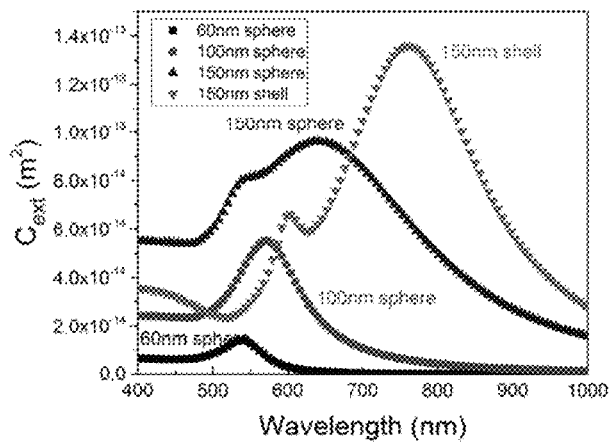
FIG. 24A is a graph comparing the extinction cross section ($C_{ext}=C_{sca}+C_{abs}$) for 60 nm nanosphere, 100 nm nanosphere, 150 nm nanosphere and 150 nm nanoshell.
Figure 24B:
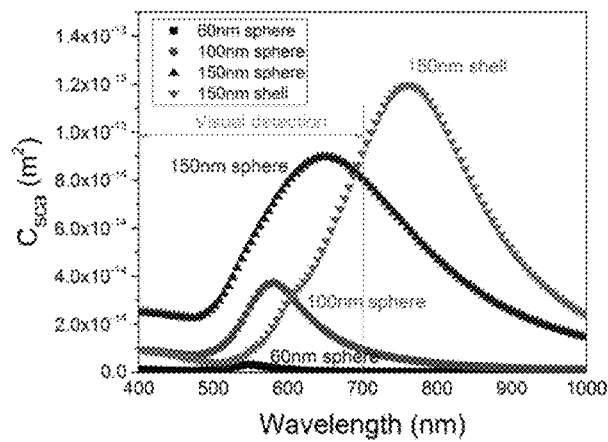
FIG. 24B is a graph comparing the scattering cross-section in the visible region for 60 nm nanosphere, 100 nm nanosphere, 150 nm nanosphere and 150 nm nanoshell.
Figure 24C:
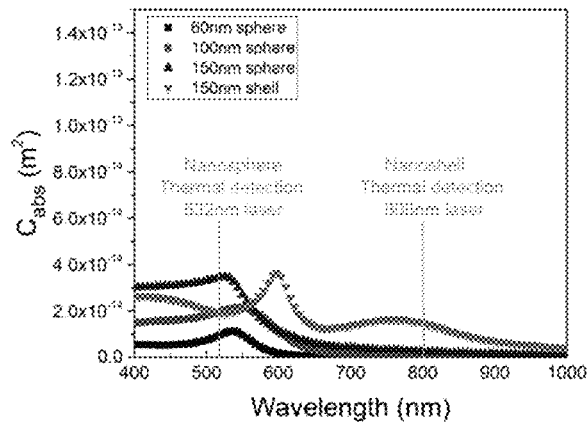
FIG. 24C is a graph comparing the absorption cross section at laser excitation wavelength for 60 nm nanosphere, 100 nm nanosphere, 150 nm nanosphere and 150 nm nanoshell.

Nanospheres and nanoshells of the same size (150 nm) were quantitatively compared. The optical properties were first compared of 150 nm nanosphere and 150 nm nanoshell (FIGS. 24A-24C), and predict that 150 nm nanosphere has lower visual and thermal detection limits than 150 nm nanoshell. Further, by printing 150 nm nanospheres and 150 nm nanoshells onto membrane, we found 150 nm nanosphere is superior to 150 nm nanoshell both in visual detection and thermal detection (FIG. 22).

Figure 22:
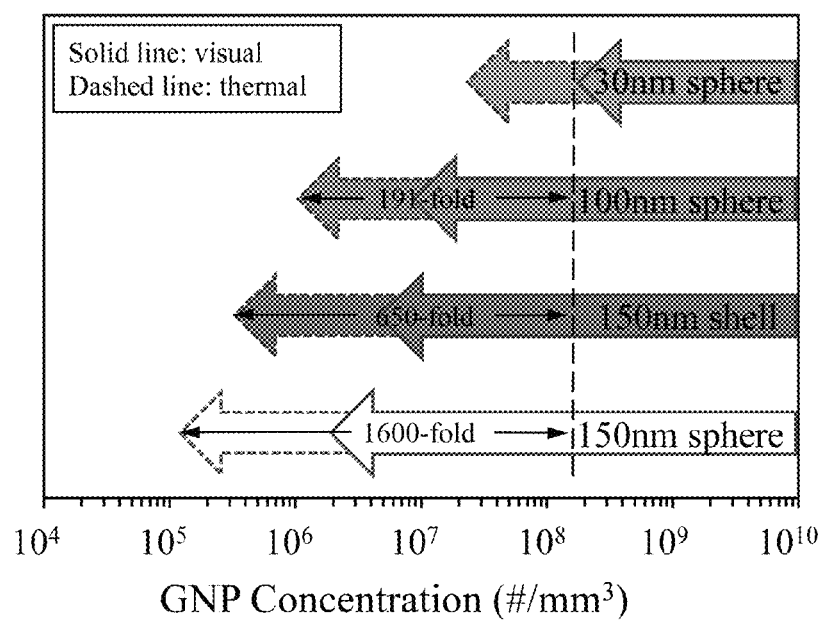
FIG. 22 is a graph of experimental results of thermal and visual detection limits of 30 nm nanospheres, 100 nm nanospheres, 150 nm nanospheres and 150 nm nanoshells printed onto LFA membrane.

A 1600-fold sensitivity improvement was achieved with thermal contrast over 30 nm GNP visual contrast by using 150 nm GNPs printed into LFA membranes (FIG. 22). It was demonstrated that 150 nm nanospheres have lower detection limits than 150 nm nanoshell both in visual ($1.8 \times 10^6$ nanospheres/$m^3$ vs. $4.5 \times 10^6$ nanoshells/$m^3$) and thermal contrast detection ($1.2 \times 10^5$ nanospheres/$m^3$ vs. $2.8 \times 10^5$ nanoshells/$m^3$). Importantly, the thermal detection of 150 nm sphere showed 1600-fold improvement over visual detection of 30 nm GNP sphere and 16-fold improvement over the visual detection of a 150 nm nanosphere.

Figure 23A:
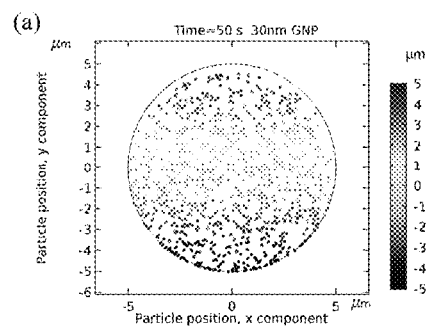
FIGS. 23A-23D are plots modeling of GNP particles settling in 5 μm radius cellulose pores over 50 sec. Specific cases for GNPs of sizes are shown, for instance: 30 nm (FIG. 23A), 60 nm (FIG. 23B), 100 nm (FIG. 23C) and 400 nm (FIG. 23D).
Figure 23B:
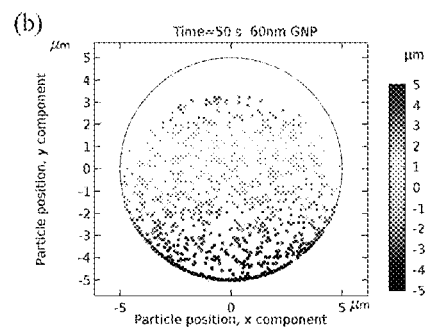
Figure 23C:
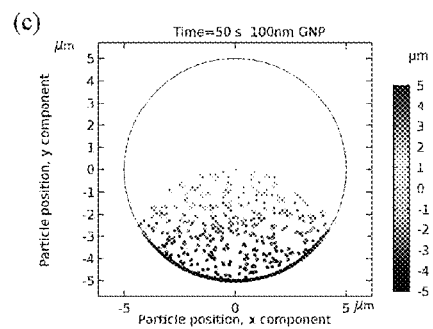
Figure 23D:
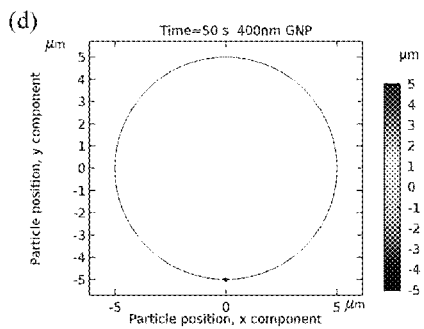

To study the settling of different sized GNPs in LFA membrane, COMSOL was used to track the position of GNPs in membrane pores (5 μm radius) over the period when a GNP travels from conjugate pad to test line (50s). Gravity, drag force and Brownian motion were included in the modeling. 1000 GNPs distributed uniformly within the pore were released at t=0. Convective velocity was set to 0.2 mm/s. The distribution of GNPs with different sizes (including 30 nm (FIG. 23A), 60 nm (FIG. 23B), 100 nm (FIG. 23C) and 400 nm (FIG. 23D)) within the pore at t=50s were compared in FIGS. 23A-23D. The results demonstrated that 400 nm GNP will settle before reaching test line, therefore will potentially decrease the sensitivity of the LFA.

Although the present description has been described with reference to embodiments, workers skilled in the art will recognize that changes may be made in form and detail without departing from the spirit and scope of the disclosure.

What is claimed is:

1. A method of enhancing the analytical performance of a lateral flow assay comprising: optimizing the size and shape of nanoparticles in a lateral flow assay, wherein the optimizing comprises analyzing the binding affinity of an analyte to the nanoparticles coated with analyte binding molecules and the diffusion and convection of the nanoparticles to a test region in a membrane of the lateral flow assay and wherein the analyzing comprises measuring the thermal response of the nanoparticles by a thermal sensor in response to an energy signal applied by an energy source and wherein the thermal sensor is an infrared sensor.

2. The method of claim 1 wherein the lateral flow assay comprises test dots in a test region.

3. The method of claim 1 wherein the concentration range of the lateral flow assay for detecting the analyte in a sample is between about $10^{-5}$ mg/L and about 310 mg/L.

4. The method of claim 1, wherein the thermal response comprises the absorption properties of the nanoparticles and the scattering properties of the nanoparticles, and wherein the absorption properties and the scattering properties determine the optimal size and shape of the nanoparticles in the assay.

5. The method of claim 1, wherein the energy source applied comprises laser excitation and the sensor comprises an infrared camera.

6. The method of claim 1, wherein the analyte in the assay is detected over a range of 3 orders of magnitude or more.

7. The method of claim 1, wherein the analyte in the assay is detected over a range of 6 orders of magnitude or more.

8. The method of claim 1, wherein the concentration range of the assay for detecting the analyte in a sample is between about 3 log 10 and about 7 log 1o.

9. The method of claim 1 wherein the nanoparticles are between about 10 nm and about 400 nm.

\* \* \* \* \*